United States Patent [19]
Kriesel

[11] Patent Number: 5,419,771
[45] Date of Patent: May 30, 1995

[54] FLUID DELIVERY APPARATUS AND SUPPORT ASSEMBLY

[75] Inventor: Marshall S. Kriesel, St. Paul, Minn.

[73] Assignee: Science Incorporated, Bloomington, Minn.

[21] Appl. No.: 129,693

[22] Filed: Sep. 29, 1993

Related U.S. Application Data

[63] Continuation-in-part of Ser. No. 69,937, May 28, 1993, Pat. No. 5,336,188, which is a continuation-in-part of Ser. No. 46,438, May 18, 1993, which is a continuation-in-part of Ser. No. 987,021, Dec. 7, 1992, Pat. No. 5,279,558, which is a continuation of Ser. No. 870,269, Apr. 17, 1992, Pat. No. 5,205,820, which is a continuation-in-part of Ser. No. 642,208, Jan. 16, 1991, Pat. No. 5,169,389, which is a continuation-in-part of Ser. No. 367,304, Jun. 16, 1989, Pat. No. 5,019,047.

[51] Int. Cl.⁶ .............................................. A61M 37/00
[52] U.S. Cl. ..................................... 604/132; 604/890.1; 128/DIG. 12; 211/86; 211/162; 222/173
[58] Field of Search ................. 128/DIG. 12; 604/82, 604/83, 85, 131–132, 151, 153, 189, 246, 257, 259, 262, 890.1; 211/86, 113, 117, 125, 162; 222/160, 173, 174, 608–610, 611.1, 180

[56] References Cited

U.S. PATENT DOCUMENTS

| | | | |
|---|---|---|---|
| 4,474,575 | 10/1984 | Eckenhoff et al. | 604/131 |
| 4,968,301 | 11/1990 | di Palma et al. | 604/132 |
| 4,969,873 | 11/1990 | Steinbach et al. | 604/93 |
| 5,176,641 | 1/1993 | Idriss | 604/133 |
| 5,248,300 | 9/1993 | Bryant et al. | 604/134 |

*Primary Examiner*—Corrine Maglione
*Attorney, Agent, or Firm*—James E. Brunton

[57] ABSTRACT

An apparatus for accurately infusing large volumes of fluids into a patient at specific rates over an extended periods of time. The apparatus includes one or more dispensers of a low profile, laminate or layered construction each having a stored energy source in the form of a distendable membrane or an elastomeric cellular mass, which in cooperation with a base, defines a fluid chamber having a fluid inlet and a fluid outlet. The apparatus further includes a support for supporting the dispensers in a coupled relationship with a manifold system which has an outlet to which an administration set can be connected. In one form of the invention, the apparatus also includes a filling vial assembly that can be coupled with the dispensers to fill the fluid chambers thereof with the fluids to be infused.

34 Claims, 13 Drawing Sheets

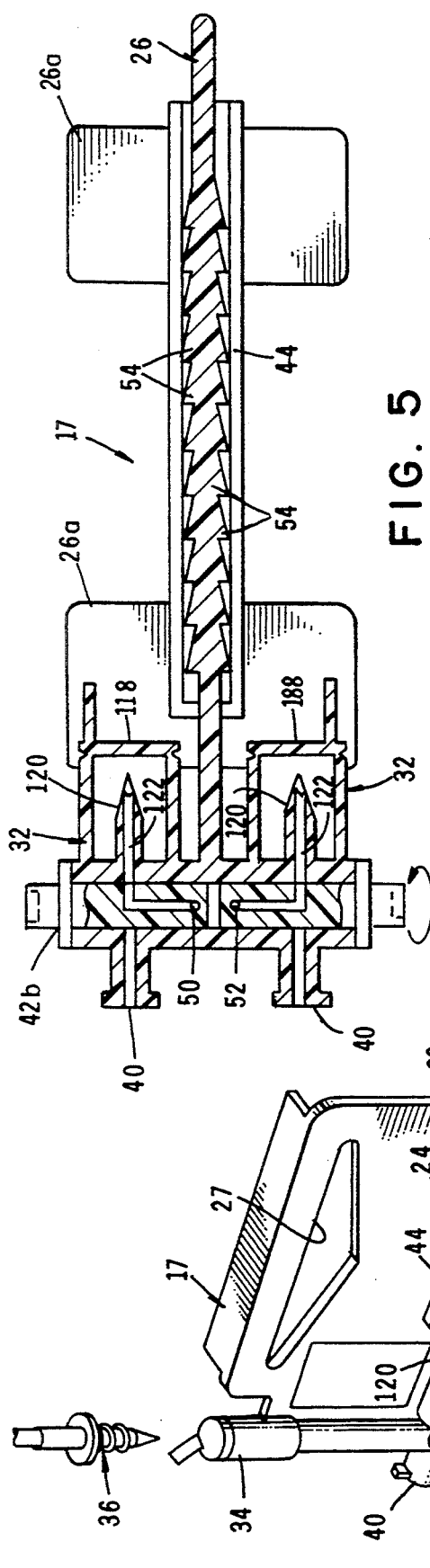
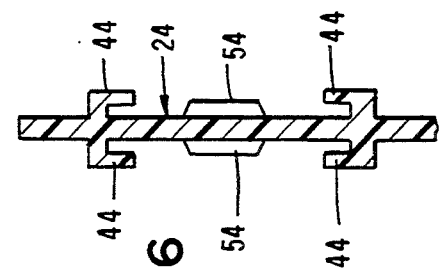
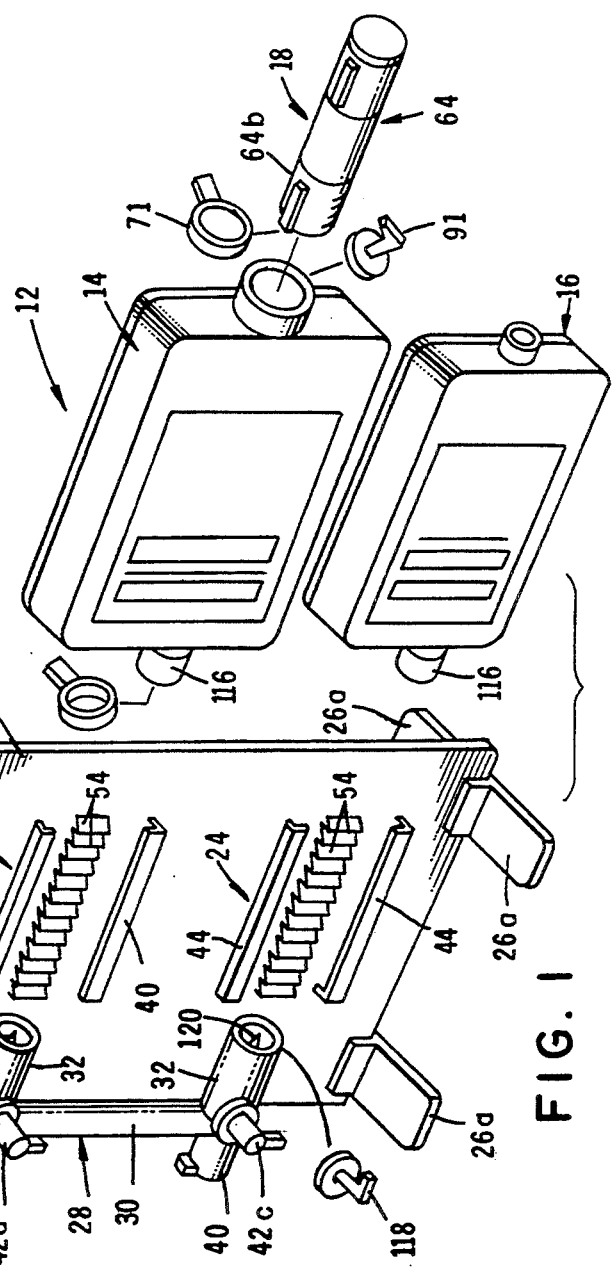

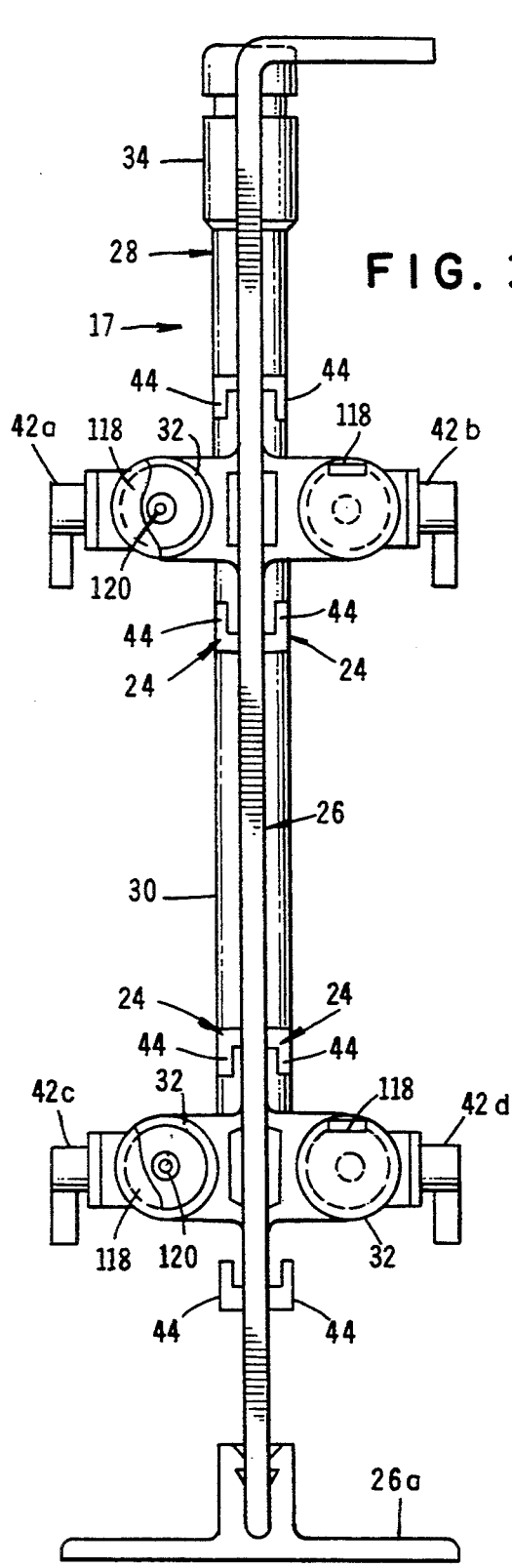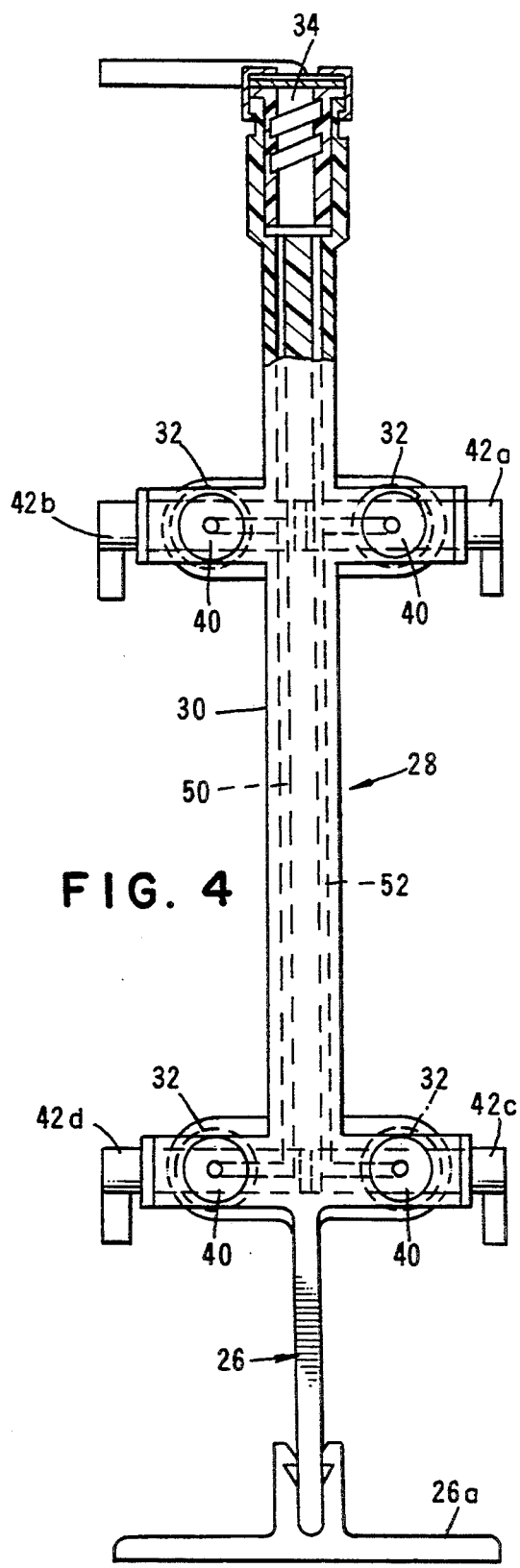

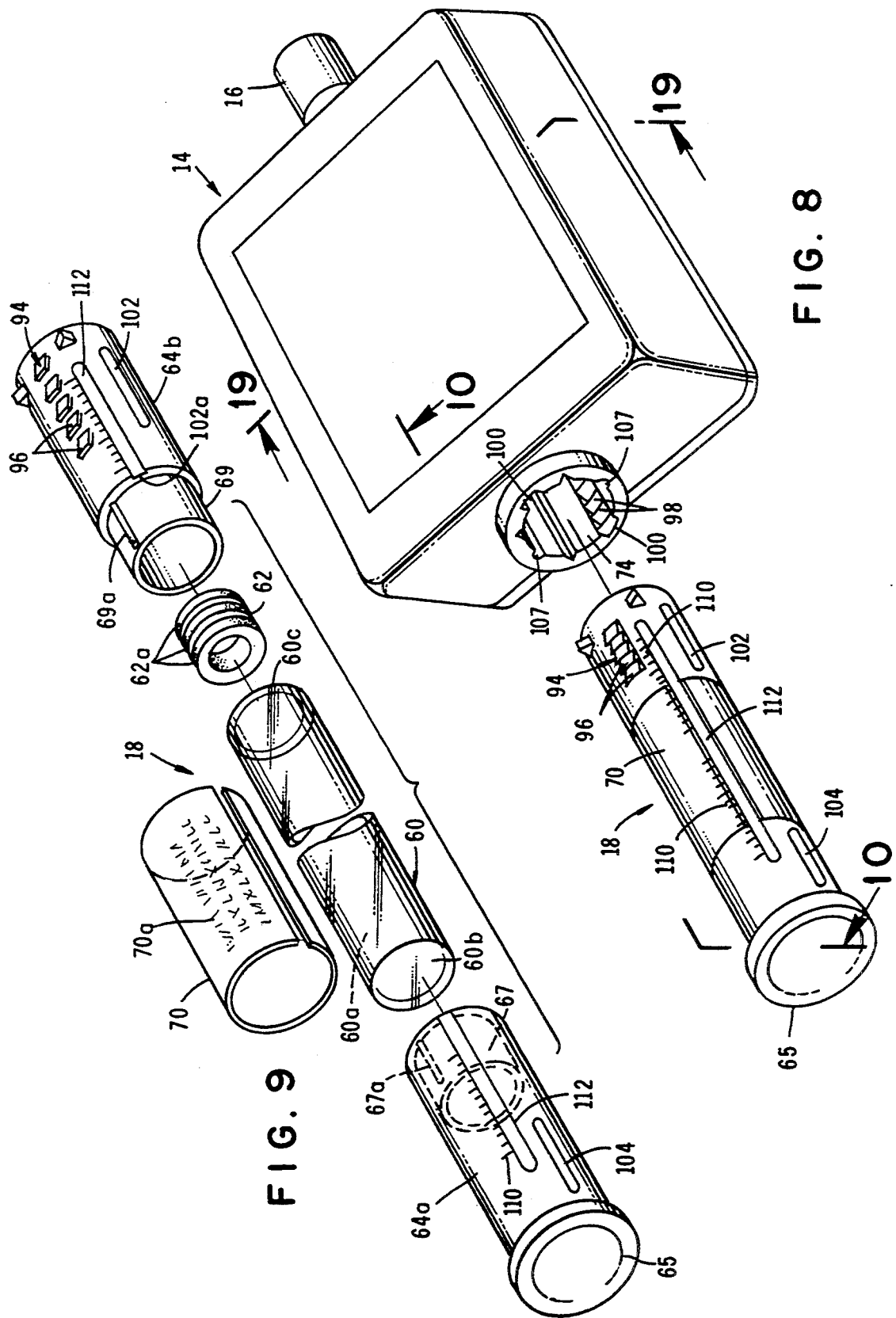

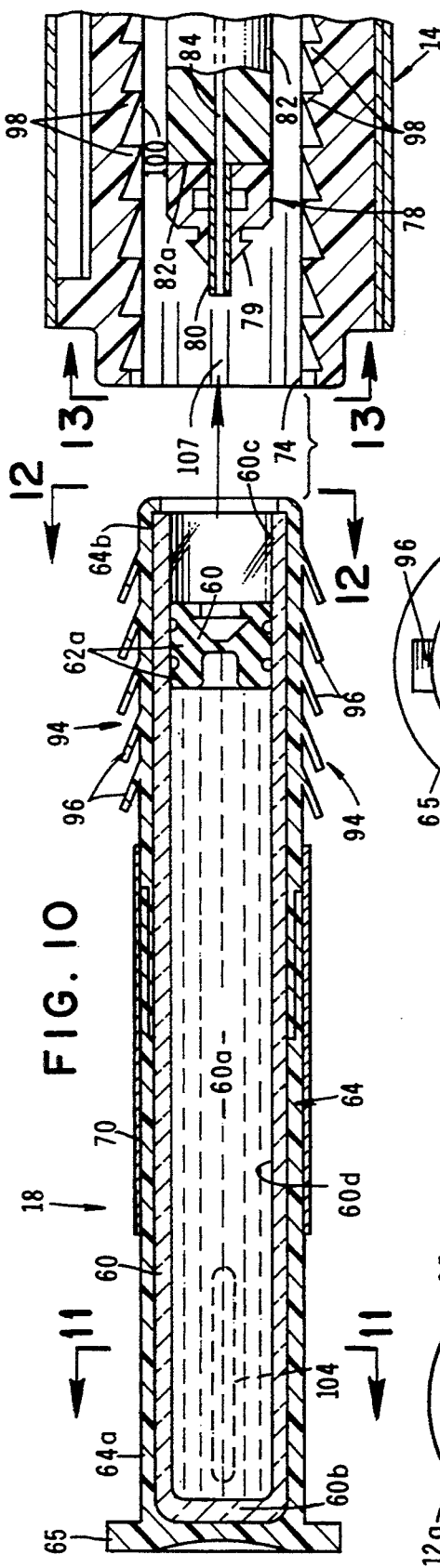
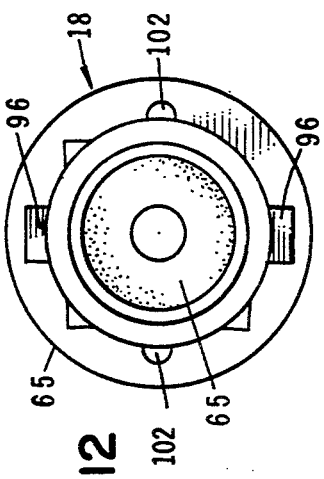
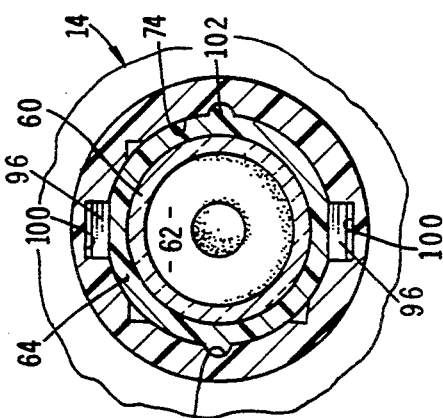
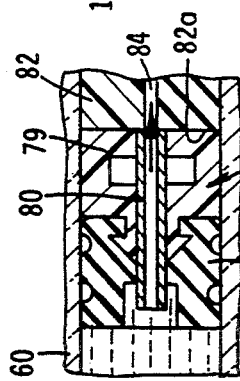
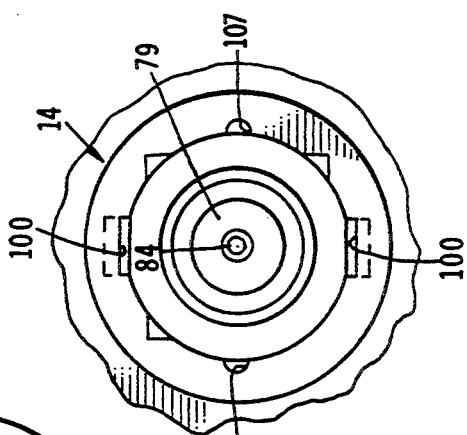
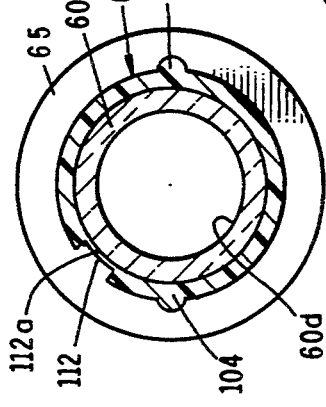

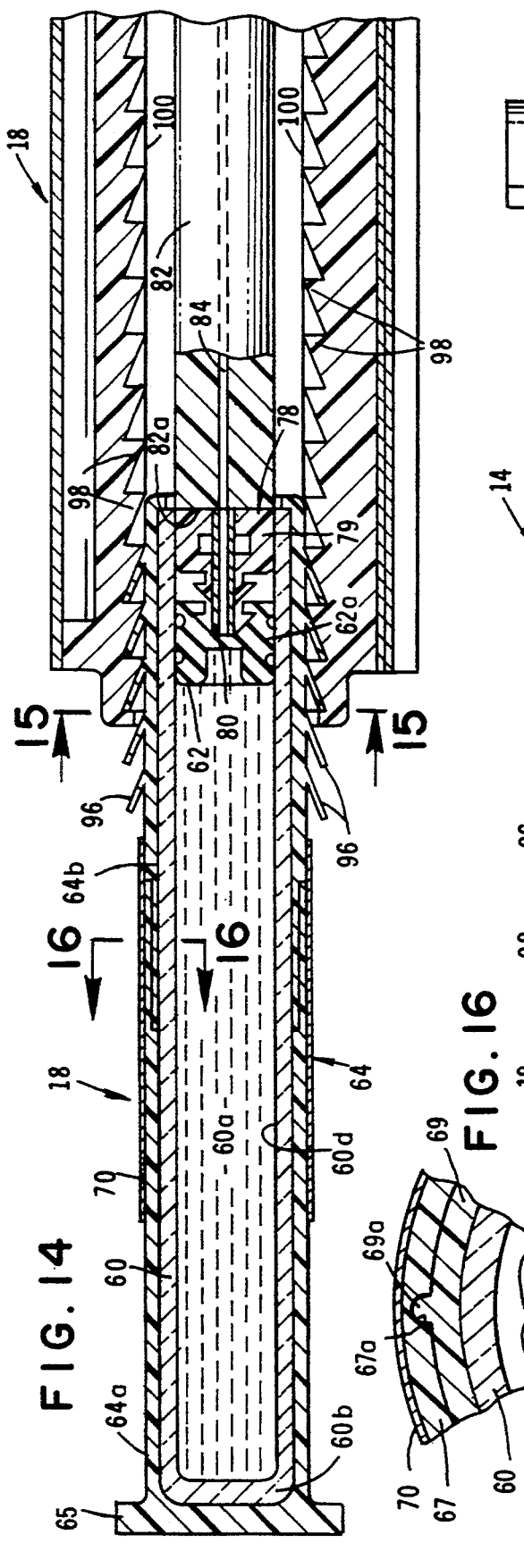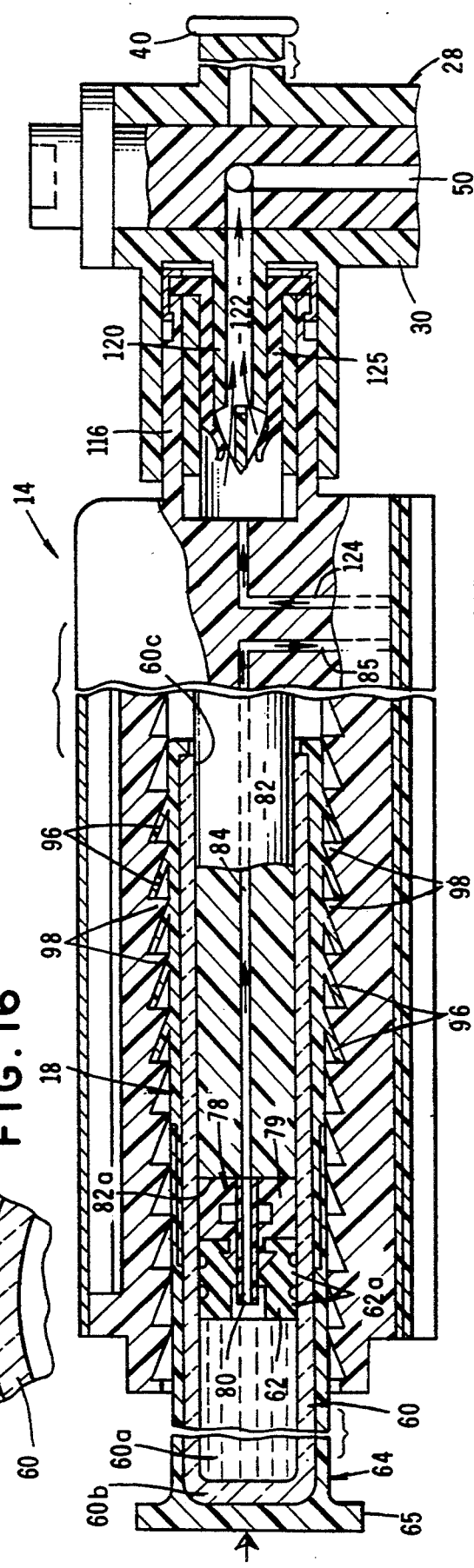

FLUID DELIVERY APPARATUS AND SUPPORT ASSEMBLY

BACKGROUND OF THE INVENTION

This is a Continuation In Part Application of application Ser. No. 08/069,937, filed May 28, 1993 which has now issued into U.S. Pat. No. 5,336,188, which is a Continuation In Part of application, Ser. No. 08/046,438, filed May 18, 1993, which is a Continuation In Part of application Ser. No. 07/987,021, filed Dec. 7, 1992, which has now issued into U.S. Pat. No. 5,279,558 and which is a continuation of application Ser. No. 07/870,269, filed Apr. 17, 1992, which has now issued into U.S. Pat. No. 5,205,820 and which is, in turn, a Continuation In Part of application Ser. No. 07/642,208, filed Jan. 16, 1991, which has now issued to U.S. Pat. No. 5,169,389 which is a Continuation In Part of application Ser. No. 07/367,304, Filed Jun. 16, 1989, which has now issued to U.S. Pat. No. 5,019,047.

FIELD OF THE INVENTION

The present invention relates generally to fluid delivery devices. More particularly, the invention concerns an improved apparatus for infusing medicinal agents into an ambulatory patient at specific rates over extended periods of time.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used in the apparatus of the present invention, as well as various alternate constructions of the apparatus, are described in detail in U. S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/046,438 filed by the present inventor on Apr. 13, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the invention described in Continuation-In-Part application Ser. No. 08/069,937 includes first and second cooperating fluid chambers both driven by unique stored energy sources. This embodiment of the invention permits two or more liquid components to be stored within the device and then controllably intermixed at the time of fluid delivery. Similarly, the multireservoir design permits flushing of one of the reservoirs and the cannula with any selected fluid. The apparatus of the present invention expands on this concept by providing a novel platform support system to which several fluid dispensers of varying volume can be operably interconnected. Ser. No. 08/069,937 is incorporated by reference as though fully set forth herein.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

A further object of the invention is to provide a low profile, fluid delivery device of laminate construction which can be manufactured inexpensively in large volume by automated machinery.

Another object of the invention is to provide a device of the character described in which fluid is dispelled from the apparatus through either an integral infusion needle, or through a luer type connector, by an internal stored energy source such as a thin, distendable membrane cooperatively associated with a thin, plate-like base.

Another object of the invention is to provide an apparatus of the aforementioned character in which the stored energy source is permeable to gases at least in one direction, whereby gases within the medicinal agent can be released from the fluid chamber and not injected into the patient.

A further object of the invention is to provide a fluid delivery device in which the internal stored energy source comprises an expandable cellular mass which cooperates with a barrier member and a base to define a fluid chamber having a fluid outlet. In this form of the invention, the expandable cellular mass controllably urges fluid within the fluid chamber outwardly of the fluid outlet of the device.

By way of summary description, the novel apparatus of the present invention permits the controlled delivery from the appartus of large volumes of the same or different fluids at controlled rates in accordance with a predetermined delivery regimen. Although each of the individual fluid dispensers of the apparatus can be of varying reservoir volumes, such as 10 to 250 milliliters, by interconnecting several of the dispensers to the unique manifolding system of the present invention, the controlled delivery over a given protocol of a substantial volume of fluids can readily be accomplished. The individual fluid dispensers of selected volumes are interconnected with the manifolding system by selectively attaching the dispensers to an easily portable mounting platform upon which the manifolding system is mounted. A convenient valving system permits the platform mounted dispensers to be opened to the manifold system in any sequence that may be desired. The outlet port of the manifolding system is, in turn, coupled with an infusion set or other fluid transfer means for controllably transferring the fluid from the delivery appartus to a patient, or to any other remote site.

In one form of the apparatus of the present invention, four fluid dispensers, each having an internal stored energy source, can be mounted on the portable platform in a back-to-back relationship. Filling means, which also comprises a part of the apparatus of the invention, can be used to fill, or charge, the reservoirs of the platform mounted fluid dispenser with any selected fluid such as a diluent or with any of a variety of beneficial agents. Through the use of the novel apparatus of the invention, multiple agents can be dispensed over time individually or in cooperation with a diluent. Additionally, a diluent can be contained within one or more of the platform-mounted dispensers to enable flushing and subsequent system priming in between the delivery of other certain agents.

A specific object of the invention is to provide an apparatus which can be used for easy transport and delivery to the patient of several different medicaments including oncolytic and antibiotic agents both in the hospital and in the alternate home care environment.

Other objects of the invention are set forth in U.S. Pat. No. 5,205,820 which is incorporated herein and will become more apparent from the discussion which follows.

BRIEF DESCRIPTION OF THE DRAWINGS

FIG. 1 is a generally perspective, exploded view of one form of the fluid dispensing apparatus of the invention in which several dispensing units of various fluid capacity can be coupled with a manifolding system to deliver several different medicaments at controlled rates over time.

FIG. 3 is an enlarged side view taken along lines 3—3 of FIG. 2.

FIG. 4 is an enlarged side view taken along lines 4—4 of FIG. 2.

FIG. 5 is an enlarged view taken along lines 5—5 of FIG. 2.

FIG. 6 is an enlarged cross-sectional view taken along lines 6—6 of FIG. 2.

FIG. 8 is a generally perspective, exploded view of one form of a dispensing unit of the invention that can be connected to the mounting platform to which a vial assembly of novel construction can be coupled for filling the reservoir of the dispensing unit.

FIG. 9 is a generally perspective, exploded view of the filling vial assembly shown in FIG. 8.

FIG. 10 is a cross-sectional view taken along lines 10—10 of FIG. 8.

FIG. 11 is a cross sectional view taken along lines 11—11 of FIG. 10.

FIG. 12 is a view taken along lines 12—12 of FIG. 10.

FIG. 13 is a view taken along lines 13—13 of FIG. 10.

FIG. 14 is a cross-sectional view similar to FIG. 10, but showing the vial assembly initially mated with the dispenser unit.

FIG. 15 is a cross-sectional view taken along lines 15—15 of FIG. 14.

FIG. 16 is a cross-sectional view taken along lines 16—16 of FIG. 14.

FIG. 17 is a cross-sectional view similar to FIG. 14, but showing the appearance of the apparatus after the vial assembly has been advanced further into the dispenser unit, and the dispenser unit has been fully coupled with the manifold system of the delivery apparatus.

FIG. 18 is an enlarged, fragmentary, cross-sectional view of the forward portion of the vial assembly showing the cannula assembly of the dispenser unit in mating relationship with the penetrable piston.

DESCRIPTION OF THE INVENTION

Figure 2:
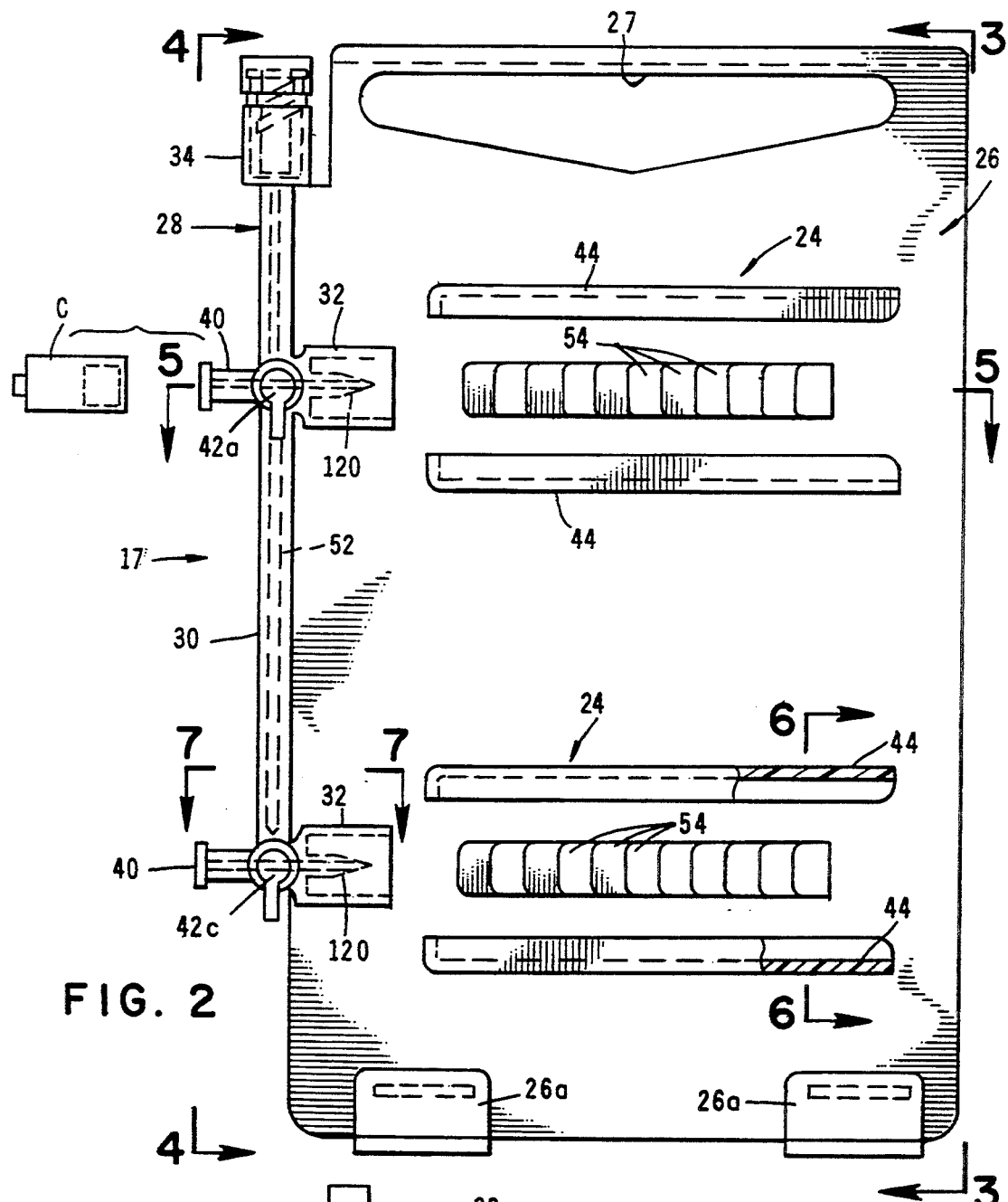
FIG. 2 is a front view of the fluid dispenser support portion of the apparatus of FIG. 1.

Referring to the drawings and particularly to FIGS. 1 through 5, one form of the apparatus of the invention is there illustrated and identified generally by the numeral 12. This apparatus comprises three major cooperating elements, namely, a plurality of fluid dispensers, such as dispensers 14 and 16, support and fluid delivery means 17 for supporting the fluid dispensers in a manner such that the fluid contained therein can be controllably delivered to a patient and filling means 18 adapted to be coupled with the fluid dispensers to fill them with selected fluids.

The fluid dispensers, such as the dispensers 14 and 16 shown in FIG. 1, are of the same general character described in the previously identified applications, Ser. Nos. 08/046,438 and 08/069,937. More particularly, each includes a base, a stored energy means for forming, in conjunction with the base, a fluid chamber and cover means receivable over the base for sealably enclosing the stored energy means. The stored energy means can comprise a distendable membrane, of the character described in U.S. Pat. No. 5,205,820 at Column 9, Lines 3-59, or alternatively, can comprise a cellular mass, or sponge-like construction of the character shown in FIG. 88 of Ser. No. 08/046,438 and identified by the numeral 975. This latter type of stored energy means is described in detail on pages 68 and 69 of the '438 application.

The cover means of the fluid dispensers 14 and 16 are of the general character shown in FIG. 1 of U.S. Pat. No. 5,205,820 and can be constructed from any of the various materials described in Columns 9 and 10 of U.S. Pat. No. 5,205,820.

Figure 23:
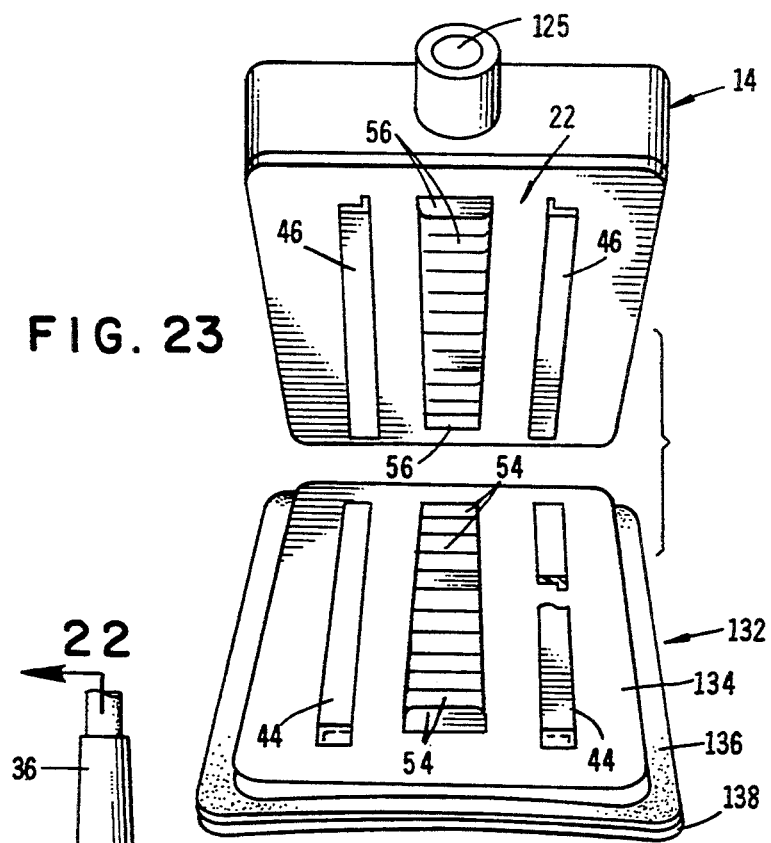
FIG. 23 is a generally perspective view of another form of the apparatus of the present invention wherein a single fluid dispenser unit is adapted to be coupled with a base that can be attached to a patient's body.

The base elements of the fluid dispensers of the present embodiment of the invention are of a slightly different construction than those described in the earlier-filed applications identified herein, in that they include base connector means 22 of the character shown in FIG. 23 for use in connecting the dispensers to the support and delivery means. In a manner presently to be described, these connector elements are matable with cooperating mounting means 24 carried by the platform 26 of the support and delivery means (FIG. 1). As best seen in FIG. 3, in addition to platform 26, the support and delivery means of this form of the invention, comprises a fluid conduit or manifold assembly 28 which is mounted along one side of platform 26.

The fluid conduit assembly of the present form of the invention comprises an elongated, tubular portion 30 having spaced apart fluid inlet ports 32 and a fluid outlet port 34 (FIG. 4) to which an infusion set or other fluid delivery means, such as one having a delivery spike 36, can be connected (FIG. 1). Also comprising a part of assembly 28 are spaced apart fluid inlet ports 40 which permit introduction of selected fluids into portion 30 of the fluid conduit assembly such as by use of a luer connector "C" or the like. Valve means shown here as valves 42a, 42b, 42c, and 42d (FIGS. 1 and 3) are provided along the length of tubular portion 30 to control fluid flow therethrough toward outlet port 34.

Turning particularly to FIGS. 2, 3 and 4, the mounting means of the apparatus can be seen to comprise four sets of platform connector means 24 with each set having two spaced apart, upstanding platform guide rails 44. Guide rails 44 slidably receive the base mounting rails 46 of the dispenser units (FIG. 23), so that the individual dispensers can be mated with the platform and then slidably advanced toward fluid conduit assembly 28 to establish fluid communication between the fluid reservoirs of the dispenser units and the internal fluid passageways 50 and 52 of the fluid conduit assembly (FIGS. 4 and 7) via the previously identified valve means. The manner by which fluid communication is established between the fluid reservoirs of the fluid dispensers and fluid passageways of the conduit assembly will be discussed in greater detail in the paragraphs which follow.

To prevent accidental separation of the fluid dispensers from platform 26 after the dispensers have been placed in fluid communication with passageways 50 and 52 of the fluid conduit assembly, novel locking means are provided. These locking means here comprise a multiplicity of upstanding locking tabs 54 which are mounted on platform 26 (FIGS. 1, 2 and 5) and a multiplicity of cooperating upstanding locking tabs 56 which are provided on the base of each fluid dispenser (see, for example, FIG. 23). As best seen in FIG. 23, flexible locking tabs 56 are disposed intermediate base mounting rails 46 of the dispensers and extend angularly therefrom in an opposite direction from that of tabs 54 so that, while the fluid dispensers can readily be advanced toward the fluid conduit assemblies, they are irreversibly locked and cannot be moved in the opposite direction. (See also FIG. 5).

Turning now to FIGS. 8 and 9, the novel filling means 18 for introducing fluid into the reservoirs of the fluid dispensers can be seen to comprise a first portion shown here as a transparent container or vial 60 having a fluid chamber 60a for containing the fluid to be added to the reservoir of the fluid dispenser. The fluid can be a diluent or any of the medicaments or beneficial agents defined in the previously identified U.S. Pat. No. 5,205,820 or other beneficial agents as may be required. Vial 60 has a closed first end 60b (FIG. 10) and a second open end 60c which is normally closed by a pierceable, piston-like plunger 62 which is movable within vial 60 from a first position shown in FIG. 10 to a second position shown in FIG. 17 and then to a third position wherein it is located proximate the closed first end of container 60. Container 60 can be a glass vial or any other suitable sterile container for containing the fluid to be used in filling the fluid dispensers.

Also forming a part of the filling means of the present embodiment of the invention is an outer casing 64 (FIG. 1), shown here as comprising cooperating first and second portions 64a and 64b (FIG. 9). First portion 64a is closed at one end by a closure wall 65 and is open at its opposite end. Provided at its open end is a socket like construction 67 which telescopically receives the open end portion 69 of second casing portion 64b. Outer casing 64 is receivable over container 60 in the manner shown in FIG. 10 and portions 64a and 64b are held in mating engagement by an adhesive bearing flexible plastic or paper overwrap 70 upon which appropriate identifying indicia 70a can be imprinted. As shown in FIGS. 9 and 16, a guide bead 69a is provided on portion 69. Bead 69a is receivable within a corresponding channel 67a provided in portion 64a to insure that portions 64a and 64b of the outer casing are properly aligned.

In a manner presently to be described, as the filling means is mated with the fluid dispenser, penetrable piston 62 is telescopically movable within container 60 from the first position shown in FIG. 14 to the second position shown in FIG. 17 and finally to a third position wherein it is disposed proximate the closed end 60b of container 60. Piston 62 is provided with a plurality of circumferentially extending sealing beads 62a which sealably engage the inner wall 60d of container 60 as the piston moves rearwardly thereof.

A tear-away-type removable cover 71 closes the second end of portion 64b (FIG. 1) until a selected fluid dispenser is to be filled (see FIG. 9). After container 60 has been filled with a suitable fluid, piston 62 is inserted into the open end of the container and sealing cap 71 is emplaced over the assemblage thus formed so as to maintain the piston and the filling fluid in a sterile, sealed condition until time of use.

Figure 7:
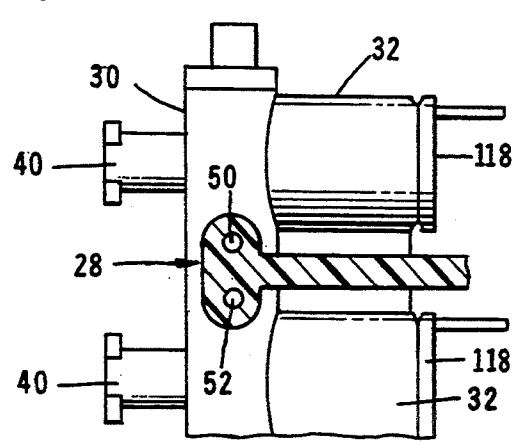
FIG. 7 is an enlarged cross-sectional view taken along lines 7—7 of FIG. 2.
Figure 19:
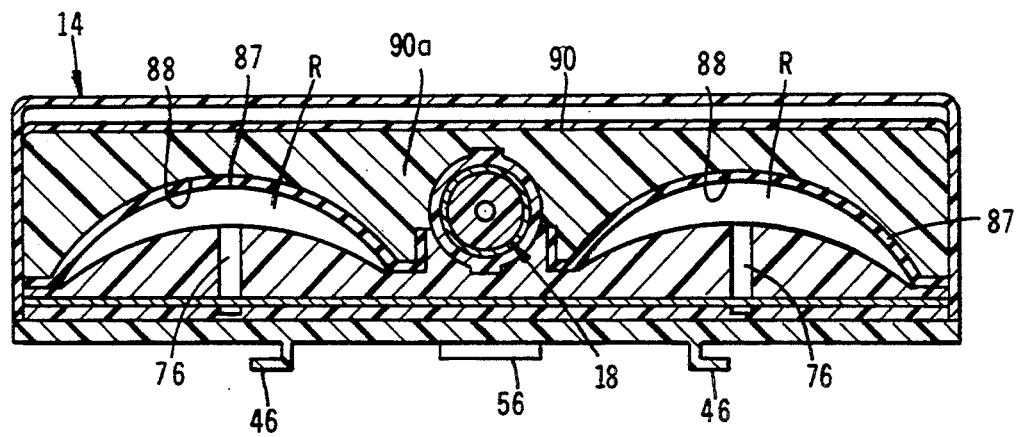
FIG. 19 is an enlarged, cross-sectional view taken along lines 19—19 of FIG. 8.
Figure 20:
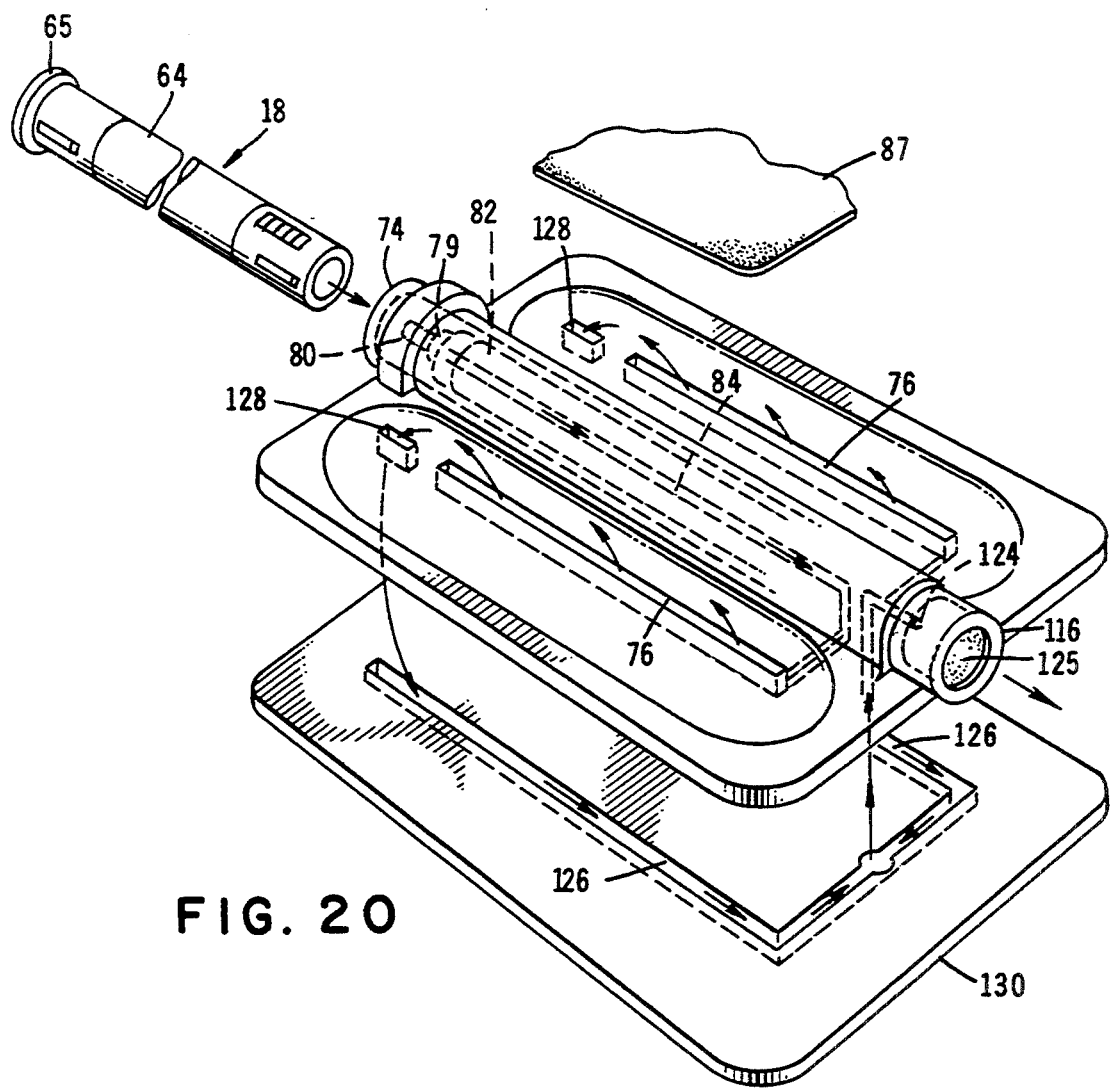
FIG. 20 is a generally perspective exploded view of the base portion of the fluid dispenser illustrating the fluid flow paths therethrough.

Turning now to FIGS. 7, 9 and 15, it is to be noted that, after the tear-away cover 71 has been removed from the filling assemblage, the second end thereof can be inserted into an inlet opening 74 provided in the dispenser unit. It is also to be noted that each dispenser unit is provided with first flow means for establishing fluid communication between the fluid inlet 76 of the reservoirs "R" of the fluid dispenser (FIGS. 19 and 20) and chamber 60a of vial 60, when the filling assemblage is mated with the fluid dispenser in the manner shown in FIG. 14. In the present embodiment of the invention, this first flow means comprises a piercing cannula assembly 78 which includes an outwardly protruding hollow cannula 80. Turning particularly to FIGS. 10 and 20, it can be seen that cannula assembly 78 also includes a housing 79 which supports hollow needle 80. Housing 79 is connected to the outboard end 82a of an elongated stem 82 which is provided with a central fluid passageway 84 that communicates with reservoirs "R" of the fluid dispenser (see FIGS. 19 and 20). With this construction, fluid flowing inwardly through the hollow cannula will flow into passageway 84 and then into the reservoirs "R" of the fluid dispenser via a connecting passageway 85 (FIG. 20) causing distendable membranes 87 to further distend outwardly to a position proximate the interior wall 88 of structural support 90a of cover assembly 90.

In using the apparatus of the invention, the fluid dispensers can be filled either prior to mounting them on the platform of the delivery system or after they have been mounted on platform 26. It is to be noted that dispenser 16 (FIG. 1) is fillable via septum port 16a by a suitable syringe assembly. Dispenser 14, on the other hand, is fillable by means of filling assembly 18. During the filling of dispenser 14, cap 71 of the filling assembly and cap 91 and the dispenser inlet (FIG. 1) are removed and the filling assembly 18 is inserted into the dispenser inlet in the manner shown in FIG. 14. Inward pressure exerted against the filling subassembly will cause hollow cannula 80 to penetrate penetrable piston 62 of the filling assembly in the manner best seen in FIGS. 14 and 18.

Referring to FIGS. 10 through 17 it is to be observed that casing 64 of the filling subassembly is provided with two sets of circumferentially spaced rows 94 of locking members, each row comprising a multiplicity of outwardly extending, resiliently deformable locking elements 96. These locking elements, which comprise a part of the interlocking means of the invention for interlocking together the filling means and the fluid dispenser, are adapted to slide past a multiplicity of inwardly extending teeth 98 provided within oppositely disposed, longitudinally extending channels 100 formed in inlet 74 of the fluid dispenser. These teeth are so constructed and arranged as to engage elements 96 in a manner to permit insertion of the filling assembly into the dispenser inlet to lock it in place and to prevent its removal after it has been fully telescopically inserted into the inlet of the fluid dispenser in the manner shown in FIG. 17. To insure proper alignment between the filling subassembly and the inlet of the fluid dispenser, forward and rearward guide rails 102 and 104 are provided on casing 64 (see FIGS. 8, 11 and 15). As shown in the drawings, guide rails 102 and 104 are closely receivable within longitudinally extending tracks 107 provided within the inlet of the fluid dispenser (see particularly FIG. 15).

Another novel feature of the filling means of the invention resides in the provision of indicator means for indicating the volume of fluid remaining within vial 60 as the vial is inserted into the inlet of the fluid dispenser. This indicator means here comprises a multiplicity of indicating indicia 110 disposed adjacent a longitudinally extending viewing slot or window 112 provided in casing 64 (FIG. 8). Since the base of the viewing window 112a (FIGS. 9 and 11) and the vial 60 are transparent, the amount of fluid remaining within the vial at any point in time can readily be determined by merely aligning one of the indicia markings on the casing with the inboard extremity of piston 62 as it moves toward its third innermost position.

As previously mentioned, the fluid dispensers can be coupled with the support and delivery means either before or after they are filled. The coupling is accomplished by first inserting the base mounting rails 46 of the dispenser into the platform guide rails 44 mounted on the platform 26. Next, the dispensers are urged forwardly toward inlet ports 32 of the manifold system. As indicated in FIGS. 1 and 2, each of the inlet ports 32 of the manifold system comprises a socket-like structure that is adapted to telescopically receive the outlet port structure 116 provided on each of the fluid dispensers.

Turning to FIG. 5, it is to be noted that each of the inlet ports 32 of the manifold system is sealed by a tear away cap 118. Removal of the tear away cap 118 exposes a piercing member 120 which has a central fluid passageway 122 that communicates via the valve means with one of the fluid passageways 50 or 52 provided within central portion 30 of the manifold assembly 28. When the fluid dispenser is coupled with the support platform in the manner shown in FIG. 17, piercing member 120 will pierce the pierceable closure membrane 125 of outlet port 116 of the dispenser thereby placing fluid passageway 122 in communication with fluid outlet passageway 124 of the fluid dispenser. As best seen in FIG. 20, passageway 124, in turn, communicates with reservoirs "R" of the fluid dispenser via flow channels 126 provided in base assembly 130. Closure membrane 125 can be any type of non-coring, penetrable membrane such as either the cup-like structure shown in FIG. 17 or, alternatively, a pierceable rubber septum of conventional construction.

After the fluid dispensers have been coupled to the support and delivery means and filled with the fluid to be delivered to the patient, the apparatus can be easily transported by grasping the platform 26 using finger opening 27. Actual delivery to the patient and priming of the fluid administration set can be accomplished through the selective operation of the valve means. For example, with the loaded platform supported on feet 26a in the upright configuration shown in FIG. 1, opening of valve 42a will permit the fluid contained within dispenser 14 to be delivered to the patient via delivery spike 36. Similarly, by opening valve 42c, the fluid contained within dispenser 16 can likewise be delivered to the patient. In similar manner, the fluids contained within the fluid dispensers mounted on platform 26 in a back-to-back relationship with dispensers 14 and 16 can be delivered to the patient by selectively opening valves 42b and 42d (see FIG. 3). It is to be appreciated that fluid delivery from each of the dispensers can be controlled by operation of the valve means. Similarly, fluid from two or more of the dispensers can be delivered simultaneously by operation of the valve means.

It is also to be appreciated that, since the fluid dispensers can contain different medicinal fluids in different volumes, a number of different delivery protocols can be achieved over varying periods of time. For example, dispenser 14 can have a volume of 30 milliliters and can contain a first medicament, while dispenser 16 can have a volume of 20 milliliters and can contain a second medicament. In like manner, the dispensers mounted back to back on platform 26 with dispensers 14 and 16 can be of varying volumes and can contain diluents or any of a number of other selected medicaments. Thusly, by way of example, up to 30 milliliters of a first fluid can be delivered at a first rate followed by delivery of up to 20 milliliters of a second fluid at a second rate. If desired, further delivery of fluids from the remaining two dispensers can be concurrently delivered (by way of example, a diluent) or can be intermittently used to prime and flush the system. In this way, large volumes of fluids can be delivered from the apparatus, as for example the administration of an oncolytic medicament protocol together with a keep vein open (kvo) requirement as would be used for certain extended term cell specific and cell cycle specific chemotherapy delivery regimes. The types of fluids delivered to the patient can be widely varied or large volumes of the same fluid can be delivered. Additionally, wide varieties of other fluids can be introduced into passageways 50 and 52 via the luer connector ports 40. For other applications, ports 40 can comprise septal ports which permit introduction of fluids into passageways 50 and 52 by means of a syringe. Thus the treatment protocols can be virtually unlimited.

Rather than coupling the fluid dispensers to the support and delivery means 17, any one of the dispensers, as for example, dispenser 14, can be coupled with a body attachment base assembly 132 of the character shown in FIG. 23. Base assembly 132 comprises a plate-like platform 134 to which platform guide rails 44 and locking tabs 54 are mounted. As before, rails 44 slidably receive base mounting rails 46 of the fluid dispenser and tabs 54 lockably engage tabs 56 of the fluid dispenser as the units are operably interconnected.

Body attachment base 132 includes means for attaching the apparatus to the patient's body, which may comprise VELCRO web-type attachments or any other suitable attachments such as belt or clothing clips. The attaching means is here shown as comprising a sponge-like pad 136 that is connected to the undersurface of base 134 by any suitable means. An adhesive material is provided on the undersurface of pad 136 to enable the dispenser to be connected to the patient's body. This adhesive material is covered by a peel strip 138 until time of use. After the selected fluid dispenser has been coupled with the body attachment base and the assemblage thus formed attached to the patient's body, the fluid contained within the dispenser can be delivered to the patient using any type of well known administration set of the character having a cannula adapted to pierce closure membrane 124. Such an infusion method is well known in the art and need not be described in detail herein.

Figure 22:
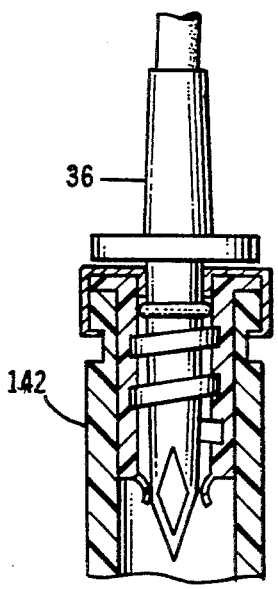
FIG. 22 is an enlarged, cross-sectional view taken along lines 22—22 of FIG. 21.
Figure 21:
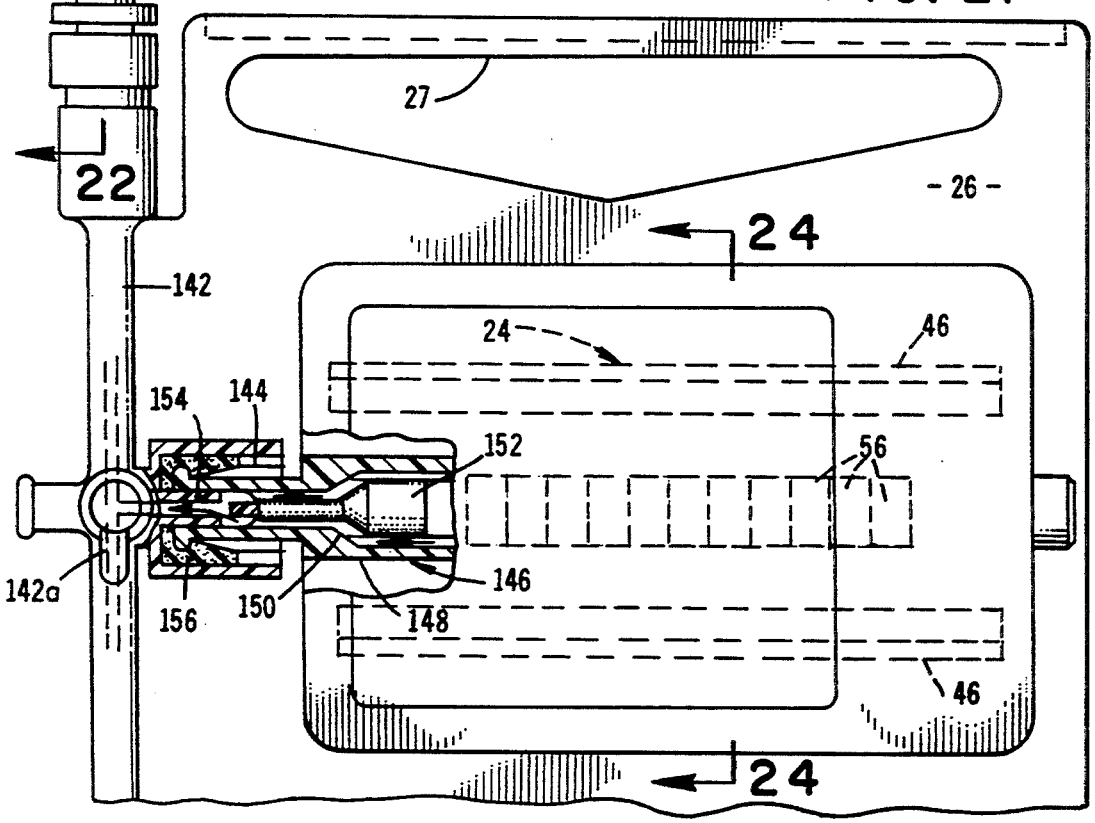
FIG. 21 is a fragmentary front view of an alternate form of the apparatus of the invention partly broken away to show internal construction.

Turning now to FIGS. 21 and 22, another embodiment of the present invention is there illustrated. This embodiment is similar in many respects to the embodiment of FIGS. 1 through 20 and like numerals are used to identify like components. The major difference between this latest form of the invention and those previously described resides in the nature of the flow control means for controlling the flow of fluids from the fluid dispenser into the fluid passageways of the manifold system 142.

As best seen in FIG. 21, the inlet ports 144 of the manifold system, rather than having a piercing spike, are each provided with valve operating means for operating a dispenser valve means carried by each of the fluid dispensers proximate the outlet thereof. The dispenser valve means here comprises a valve assembly 146 which regulates the flow of fluid outwardly from the reservoirs of the dispenser into the manifold system 142. Valve assembly 146 includes a valve body 148 which is mounted proximate the outlet of the dispenser. Body 148 is provided with a valve seat 150 and a valve member 152 which is movable from a first position in sealing engagement with the valve seat to the second valve open position shown in FIG. 21. Valve member 152 is movable into the second, open position by an operating member 154 which forms a part of the valve operating means that is carried within the manifold inlets 156 in the manner shown in FIG. 21.

The fluid dispensers of this latest embodiment of the invention are coupled with platform 26 of the support and delivery means in the manner previously described through use of mating rails 44 and 46. Similarly, each of the dispensers is locked in place on the platform by cooperating locking tabs 54 and 56. As each dispenser is coupled with platform 26, the outlet port of the dispenser is received within socket-like inlet port 156 of the manifold system and valve operating member 154 automatically moves valve member 152 inwardly into the open position. In this valve open position, fluid is free to flow from the reservoirs of the fluid dispenser via passageways 126 and 124 (FIG. 20) into valve body 148 and then, as indicated by the arrows in FIG. 21, past valve member 152 and into the internal passageway of the manifold system. The various manifold valves 142a, 142b, 142c, and 142d, which are of the character previously described, are then operated to permit the fluid contained within the fluid dispensers that are coupled with platform 26 to be controllably delivered to the patient via the delivery spike 36 (FIG. 22) of the administration set.

Figure 25:
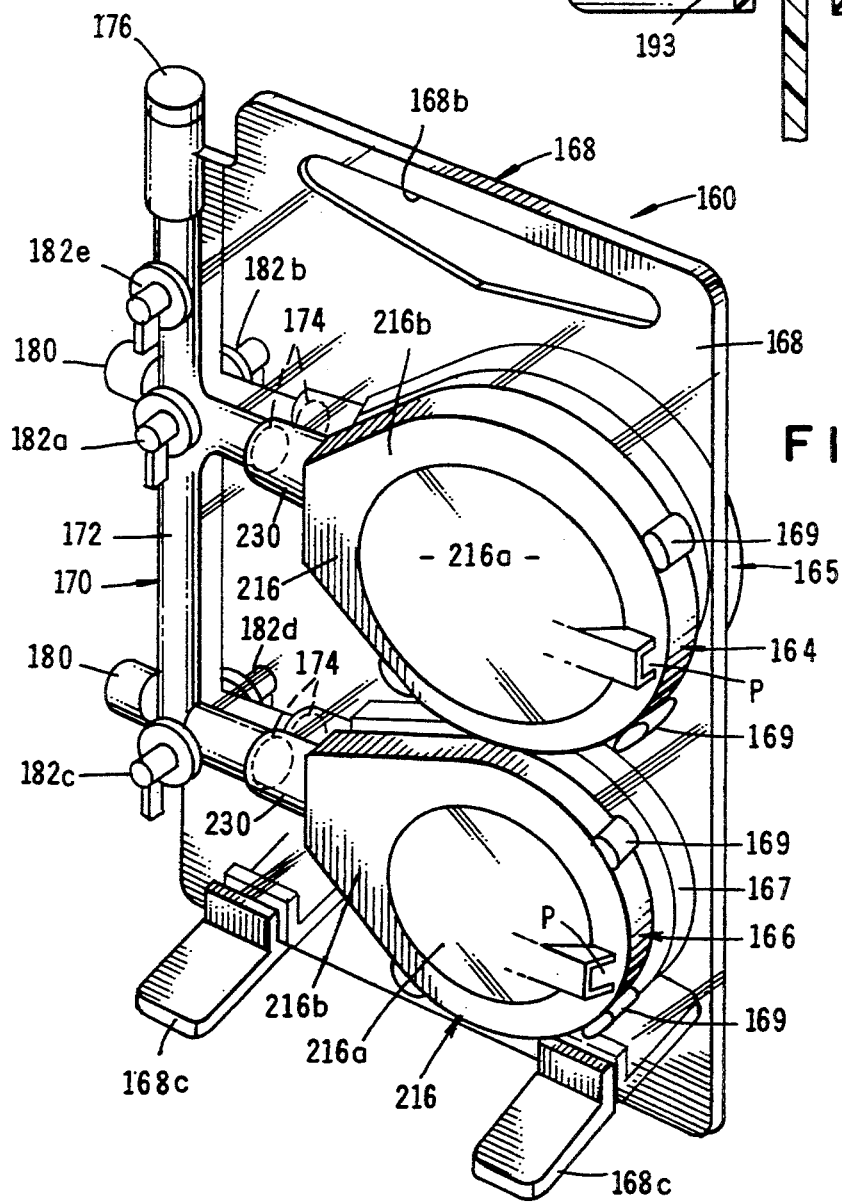
FIG. 25 is a generally perspective view of still another embodiment of the invention.

Turning now to FIG. 25, still another embodiment of the invention is there shown and generally identified by the numeral 160. This apparatus is somewhat similar to that illustrated in FIG. 1 in that it comprises a plurality of fluid dispensers, such as dispensers 164, 165, 166 and 167 and a support and fluid delivery means 168 for supporting the fluid dispensers in a manner such that the fluid contained therein can be controllably delivered to a patient.

As before, each of the fluid dispensers includes a base, a stored energy means for forming, in conjunction with the base, a fluid chamber and a cover means which is receivable over the base for sealably enclosing the stored energy means. As before, the stored energy means here comprises a distendable membrane, of the general character described in U.S. Pat. No. 5,205,820 at Column 9, Lines 3–59.

Figure 27:
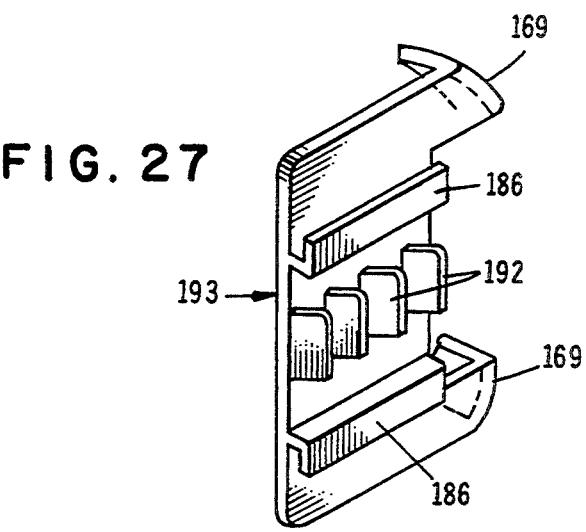
FIG. 27 is a generally perspective view of the connector element of this latest form of the invention for connecting the fluid dispenser to the platform of the delivery system.

Associated with each of the fluid dispensers of the invention, are adapter means of the character shown in FIG. 27 for use in securing the dispensers to the support and delivery means. These adapter means are matable with cooperating mounting means carried by the platform 168a of the support and delivery means (FIG. 25) and include circumferentially spaced dispenser engaging ears 169 which lockably engage the periphery of the dispensers in the manner shown in FIG. 25. In addition to platform 168a, the support and delivery means of this form of the invention, comprises a fluid conduit or manifold assembly 170 which is mounted along one side of platform 168a.

The fluid conduit assembly of the form of the invention shown in FIG. 25 is of similar construction to that shown in FIGS. 1–7 and comprises an elongated, tubular portion 172 having spaced-apart fluid inlet ports 174 and a fluid outlet port 176 to which an infusion set or other fluid delivery means can be connected in the manner previously described in connection with the apparatus shown in FIG. 1. Also comprising a part of assembly 170 are spaced apart fluid inlet ports 180 which permit introduction of selected fluids into the fluid passageways 173 and 175 (FIG. 29) of portion 172 of the fluid conduit assembly such as by use of a luer connector or the like. Ports 180 can also be septum ports adapted for use with needle syringes. Valve means, shown here as three-way valves 182a, 182c, 182d and 182e (FIGS. 25 and 32) are provided along the length of tubular portion 172 to control fluid flow therethrough toward outlet port 176. As before a valve 182b is disposed in a back-to-back relationship with valve 182a.

Figure 24:
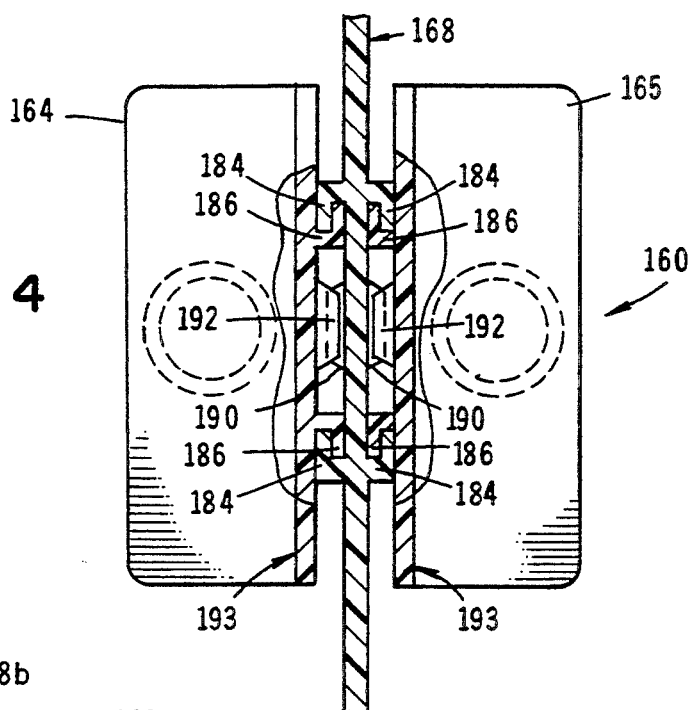
FIG. 24 is a cross-sectional view taken along lines 24—24 of FIG. 21.
Figure 26:
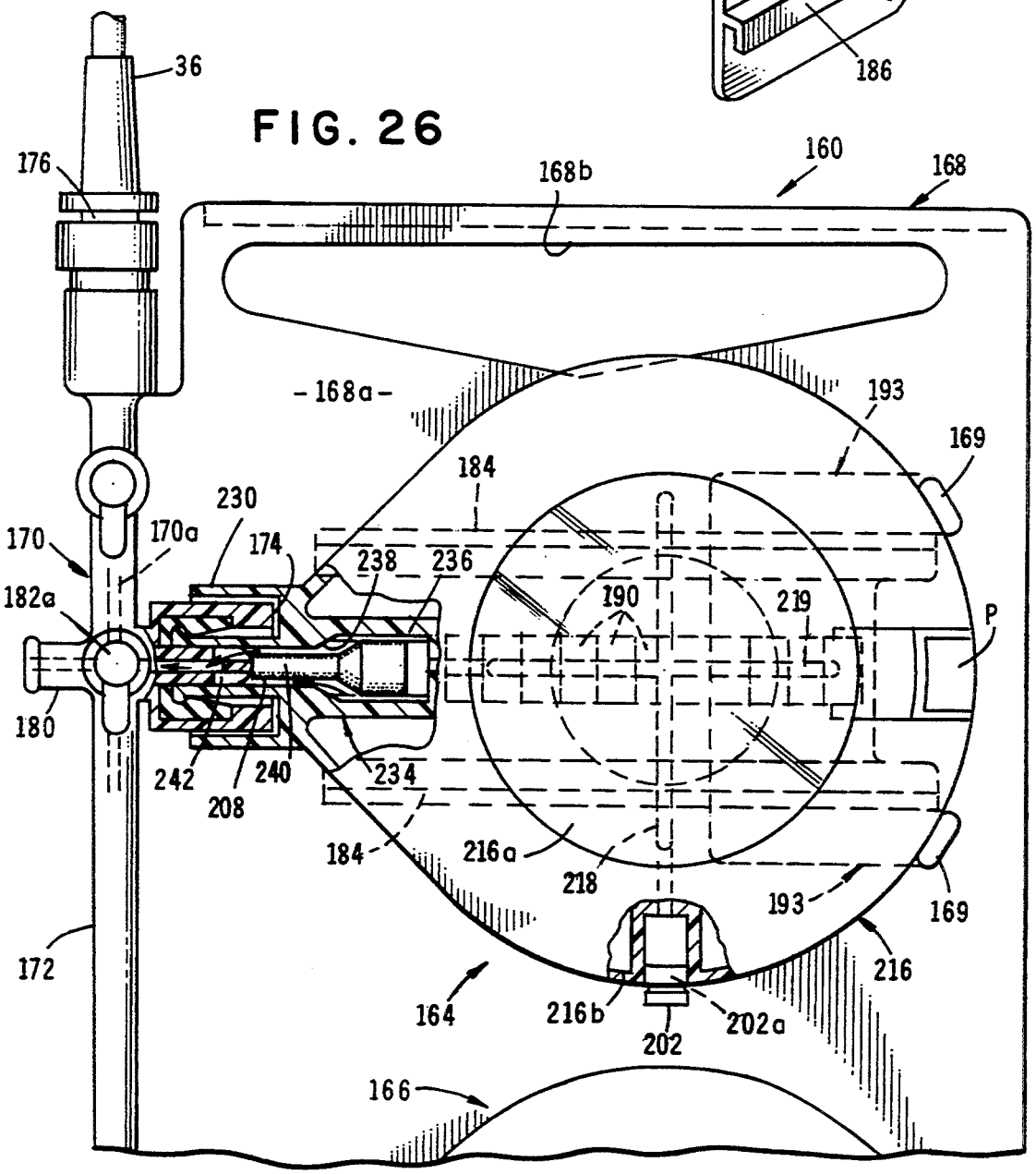
FIG. 26 is a fragmentary front view of the upper portion of the apparatus shown in FIG. 25, partly broken away to show internal construction.
Figure 32:
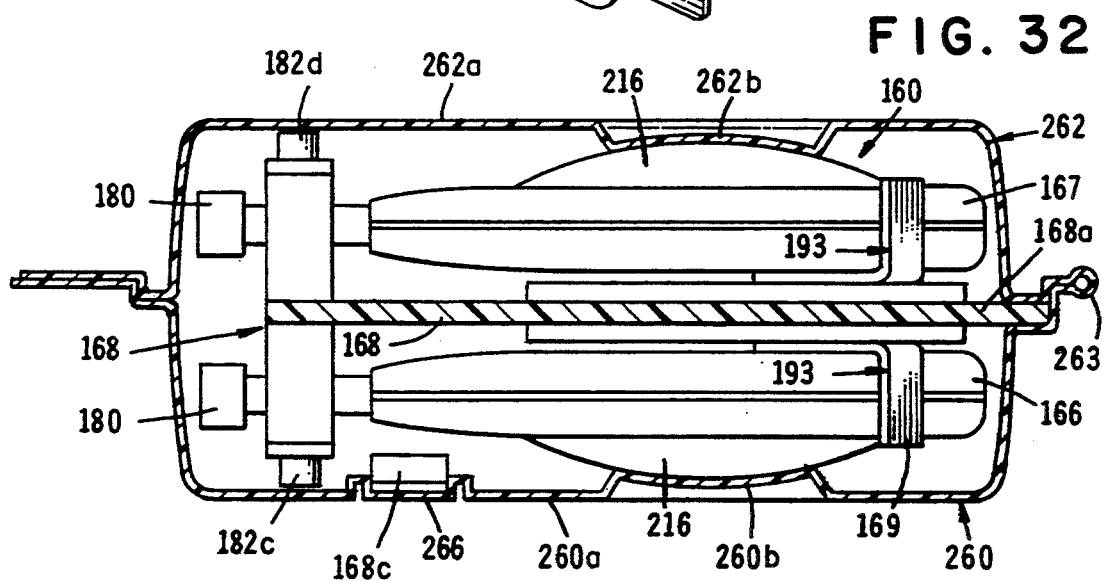
FIG. 32 is a cross-sectional view taken along lines 32—32 of FIG. 31.

Turning particularly to FIGS. 26 and 32, as before, the mounting means of the apparatus as before comprises four sets of platform mounting means. Each set of mounting means is of the construction shown in FIGS. 24 and 26 and includes two spaced-apart, upstanding platform guide rails 184. Guide rails 184 slidably receive the base connecting rails 186 of the adapter means (FIG. 27), so that the individual dispensers can be secured to the platform 168a after fluid communication has been established between the fluid reservoirs of the dispenser units and the internal fluid passageway of the fluid conduit assembly 170. Assembly 170 is provided with a single fluid passageway 170a which is located in the manner shown in FIG. 26. The manner by which fluid communication is established between the fluid reservoirs of the fluid dispensers and fluid passageway of the conduit assembly will be discussed in greater detail in the paragraphs which follow.

Figure 28:
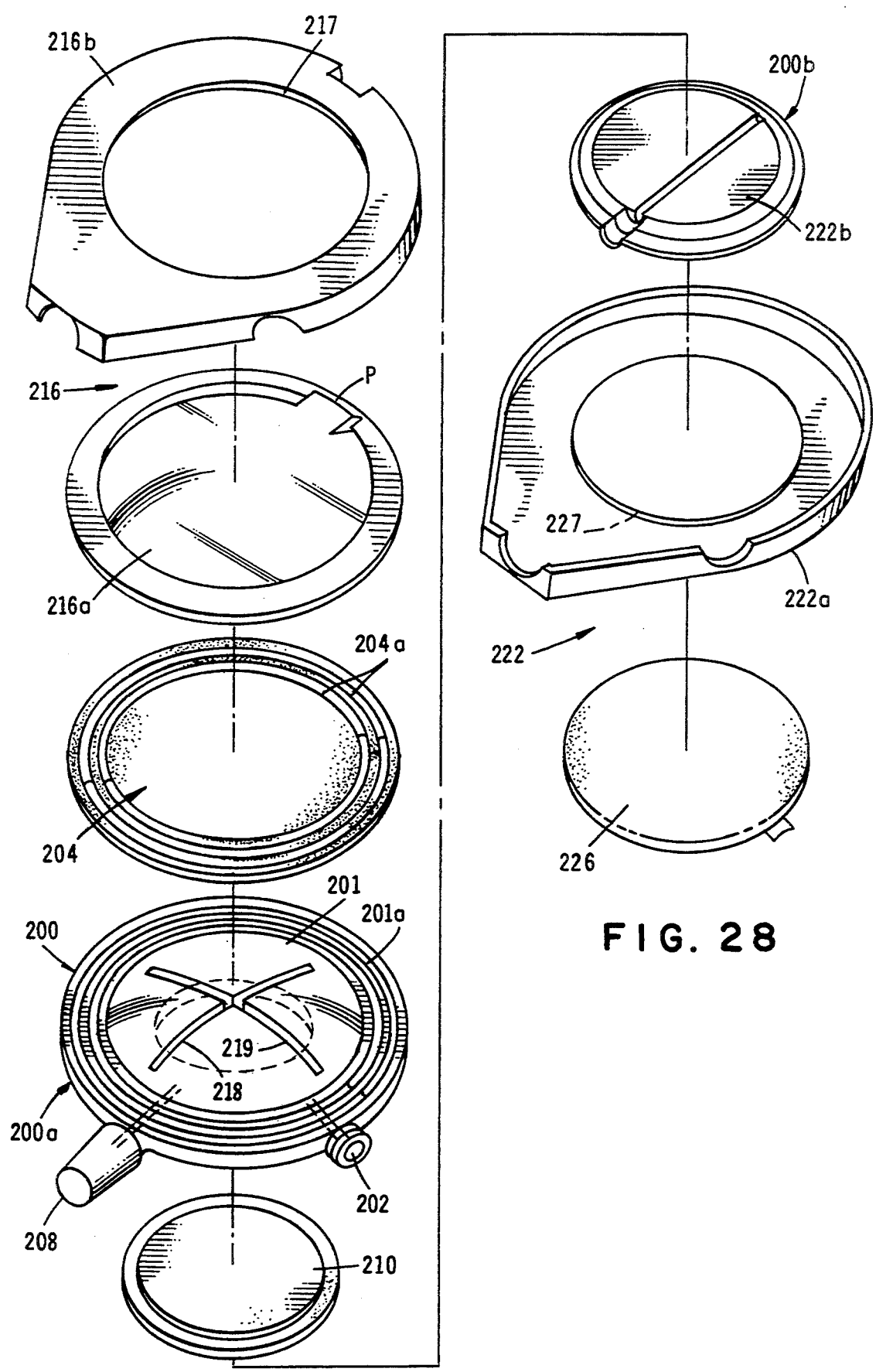
FIG. 28 is a generally perspective, exploded view of the fluid dispenser of this latest form of the invention.
Figure 29:
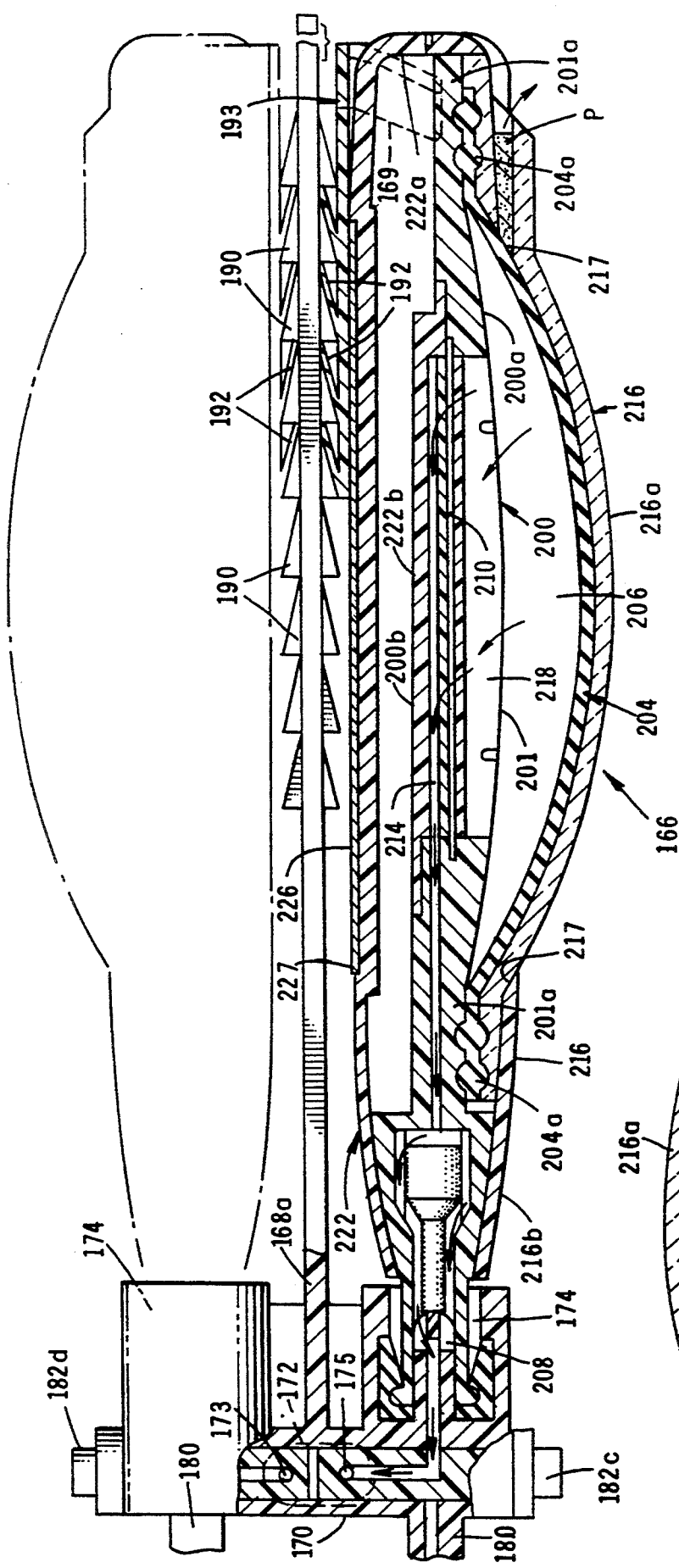
FIG. 29 is an enlarged cross-sectional view of the assembled fluid dispenser shown in a coupled relationship with the platform and manifold of the delivery system.

To prevent accidental separation of the fluid dispensers from platform 168a after the dispensers have been placed in fluid communication with the passageway of the fluid conduit assembly, locking means of the general character previously described are provided. These locking means here comprise a multiplicity of upstanding locking tabs 190 which are mounted on platform 168 (FIG. 26) and a multiplicity of cooperating upstanding locking tabs 192 which are provided on each of the connector adapters of the character shown in FIG. 27 and identified by the numeral 193. Locking tabs 192 are disposed intermediate the base mounting rails 186 of the adapters and extend angularly therefrom in an opposite direction from that of platform tabs 190 so that, while the adapters can readily be advanced toward the fluid conduit assembly as the tabs 192 deform, they cannot be retracted in the opposite direction. As indicated in FIG. 26, as the adapters are advanced toward the fluid conduit assembly, each ear 169 will engage the fluid dispenser thereby irreversably locking it in a secure coupling relationship with the fluid conduit Referring now particularly to FIGS. 28 and 29, the fluid dispenser of this latest form of the invention is of unique construction and comprises a layered structure made up of a plurality of cooperating components. As best seen by referring to FIG. 28, the dispenser here comprises a generally circular base assembly 200, having an inlet, or fill port 202. The stored energy means is here provided as a thin, generally circular shaped, prestressed distendable elastomeric membrane, or member, 204 which cooperates with base assembly 200 to form a fluid chamber 206 (FIG. 29). Base assembly 200 is made up of two cooperating portions 200a and 200b (FIG. 28) the function of which will presently be described. Member 204 is distendable outwardly in the manner shown in FIG. 29 by the introduction of fluid into the chamber under pressure via inlet port 202. As the distendable member 204 distends further outwardly, internal stresses are formed in the member which continuously urge it to return toward its less distended, original, prestressed configuration.

An optional feature of the fluid dispenser of this latest form of the invention comprises flow control means for controlling the rate of fluid flow through the outlet port 208 formed in base assembly 200. In the embodiment of the invention shown in FIG. 28, the flow control means is provided in the form of a thin, permeable member 210 which is located between chamber 206 and outlet port 208 in the manner shown in FIG. 29. The character of this flow control means is as described in U.S. Pat. No. 5,205,820 starting at Column 8, Line 43. Member 210 precisely controls the rate of fluid flow from chamber 206 into fluid conduit 214 which, in turn, communicates with outlet port 208. It is this precise control of the rate of fluid flow toward outlet 208 that enables infusion into the patient of medicinal fluids at an extremely precise rate over extended periods of time ranging from several hours to in excess of 24 hours.

Superimposed over flow control member 210 is a distendable membrane engagement means. This means comprises a part of the first portion 200a of the base assembly and includes a generally dome-shaped protuberance 201 having a peripheral portion 201a to which the beaded peripheral portion 204a of distendable membrane 204 is sealably secured by the cover means of the invention which here comprises a top cover assembly 216. Protuberance 201 is provided with a pair of perpendicularly extending fluid passageways or conduits 218 and 219. When the apparatus is assembled in the manner shown in FIG. 29, passageways 218 and 219 are superimposed over the rate control membrane 210 with the dome-shaped protuberance 201 extending into fluid chamber 206 (FIG. 29) so as to define ullage within the chamber. A bottom cover assembly 222, which also forms a part of the cover means of the invention, sealably mates with top cover assembly 216 along the periphery thereof in the manner shown in FIG. 29 so that the base assembly, the distendable membrane and the flow control member are sealably encapsulated between the top and bottom cover assemblies.

In assembling this low profile fluid dispenser, the distendable membrane 204 is initially placed over dome-like structure 201. Upon introduction of fluid into the device via inlet port 202, the membrane is distended outwardly into engagement with the interior, concave surface of portion 216a of top cover assembly 216. Portion 216a is maintained in a clamped relationship with the top cover assembly by a second portion 216b (see also FIG. 28).

Upon opening the outlet port of the dispenser in a manner presently to be described, membrane 204 will attempt to return toward its original partially stressed configuration. This construction, where in the membrane moves toward a less distended configuration, is similar to that described in U.S. Pat. Nos. 5,019,047 and 5,169,389 issued to the present inventor. In returning toward its less distended configuration, the membrane will move toward engagement with the upper surface of dome-shaped, protuberance structure 201 and will efficiently force the fluid contained with chamber 206 uniformly outwardly through passageways 218 and 219, through flow control member 210 and thence into outlet passageway 214 of the fluid dispenser (FIG. 29).

Portion 216a of top cover assembly 216 preferably comprises a transparent, plastic cover which is maintained in a clamping relationship with membrane 204 by portion 216b. As best seen in FIG. 28, portion 216b is provided with a central aperture 217 that circumscribes the central dome shaped portion of member 216a. With this construction, the position of membrane 204 can be viewed through the transparent top cover portion 216a. Provided proximate the periphery of top cover assembly 216 is a venting means for venting gases, if any, contained within the fluids. This venting means is here shown as a porous plug "P" (FIG. 29).

Affixed to the undersurface of bottom cover assembly member 222a is a cushioning means shown here as a thin, planar shaped foam pad 226. Foam pad 226 overlays a central aperture 227 formed in member 222a and is provided with adhesive on both its upper and lower surfaces. The adhesive on the peripheral portions of upper surface of pad 226 enables the pad to be affixed to the undersurface of member 222a while the adhesive on the lower surface of the foam pad can be used to releasably affix the apparatus of the invention to the patient.

Materials usable in the construction of the base assembly, the cover assemblies and the distendable membrane are discussed in detail in previously identified U.S. Pat. No. 5,205,820 which is incorporated herein by reference.

As before the fluid dispensers can be coupled with the support and delivery means either before or after they are filled. Filling is accomplished via inlet port 202 by any convenient means such as by a filling syringe having a needle adapted to penetrate the septum 202a of the filling port (FIG. 26). Fluid injected via the septum flows into passageways 218 and 219 and distends the membrane outwardly into the configuration shown in FIG. 29.

As indicated in FIGS. 25 and 26, each of the dispenser outlet ports comprises a socket-like structure 230 that is adapted to fit over the inlet port structure 174 provided on the manifold. Disposed internally of each inlet port structure 174 is a valve operating means for operating a dispenser valve means carried by each of the fluid dispensers proximate the outlet thereof. The dispenser valve means here comprises a valve assembly 234 which regulates the flow of fluid outwardly from the reservoirs of the dispenser into the manifold system 170. Valve assembly 234 includes a valve body 236 which is mounted proximate the outlet of the dispenser. Body 236 is provided with a valve seat 238 and a valve member 240 which is movable from a first position in sealing engagement with the valve seat to the second, valve open position shown in FIG. 26. During the delivery mode, valve member 240 is movable into the second, open position by an operating member 242 which forms a part of the valve operating means that is carried within the manifold inlets 174 (FIG. 26).

The fluid dispensers of this latest embodiment of the invention are coupled with platform 168a of the support and delivery means in the manner previously described through use of mating rails 184 and 186. Similarly, each of the dispensers is locked in place on the platform by cooperating locking tabs 190 and 192. As each dispenser is coupled with platform 168a, the inlet port of the manifold system is received within socket-like outlet port 230 of the fluid dispensers and valve operating member 242 automatically moves valve member 240 inwardly into the open position. In this valve open position, fluid is free to flow from the reservoir of the fluid dispenser into the internal passageway of the manifold system via the manifold valves 182 which are of the character previously described. Appropriate operation of the manifold valves permits the fluid contained within the fluid dispensers that are coupled with platform 168a to be controllably delivered to the patient via the delivery spike 36 (FIG. 26) of the administration set in the same manner as is previously described herein.

After the fluid dispensers have been coupled to the support and delivery means and filled with the fluid to be delivered to the patient, the apparatus can be easily transported by grasping the platform 168a using finger opening 168b. Actual fluid delivery to the patient can be accomplished through the selective operation of multi-way valves 182. For example, with the loaded platform supported on feet 168c in an upright configuration as shown in FIG. 25, opening of valve 182a will permit the fluid contained within dispenser 164 to be delivered to the patient via delivery spike 36. Similarly, by opening valve 182c, the fluid contained within dispenser 166 can be delivered. In like manner, the fluids contained within the fluid dispensers 165 and 167 which are mounted on platform 168a in a back-to-back relationship with dispensers 164 and 166 can be delivered by selectively opening their respective control valves.

As before, since the fluid dispensers can contain different medicinal fluids in different volumes, a number of different delivery protocols can be achieved over time. Using the apparatus of the invention, the types of fluids delivered to the patient can be widely varied or large volumes of the same fluid can be delivered. Additionally, wide varieties of other fluids can be introduced into passageways 180 via luer connector ports, septal or the like. Thus the treatment protocols are virtually unlimited.

Figure 30:
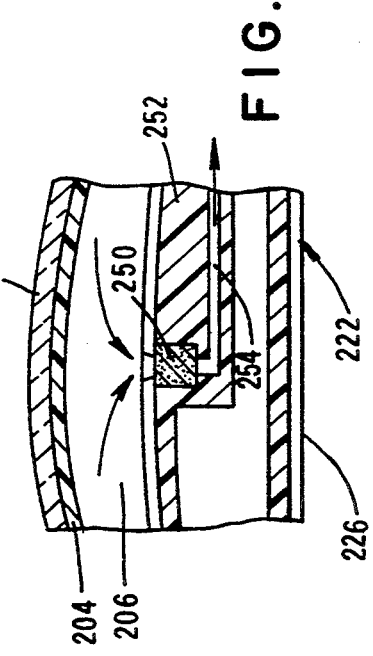
FIG. 30 is a fragmentary, cross-sectional view of a portion of still another form of fluid dispenser of the apparatus.

Turning now to FIG. 30 an alternate form of flow rate control means for controlling the rate of fluid flow outwardly from the reservoir of the fluid dispenser is there illustrated. This means is here provided as a porous or sintered member 250 which is carried by base member 252 of the base assembly. Member 250, which permits fluid flow therethrough at a predetermined rate, is disposed between reservoir 206 and outward flow passageway 254 which leads to the outlet port of the dispenser. By selecting the proper rate control member 250 having the desired diameter, effective surface area, thickness and fluid resistance, the rate of fluid flow outwardly of the dispenser can be precisely controlled.

Figure 31:
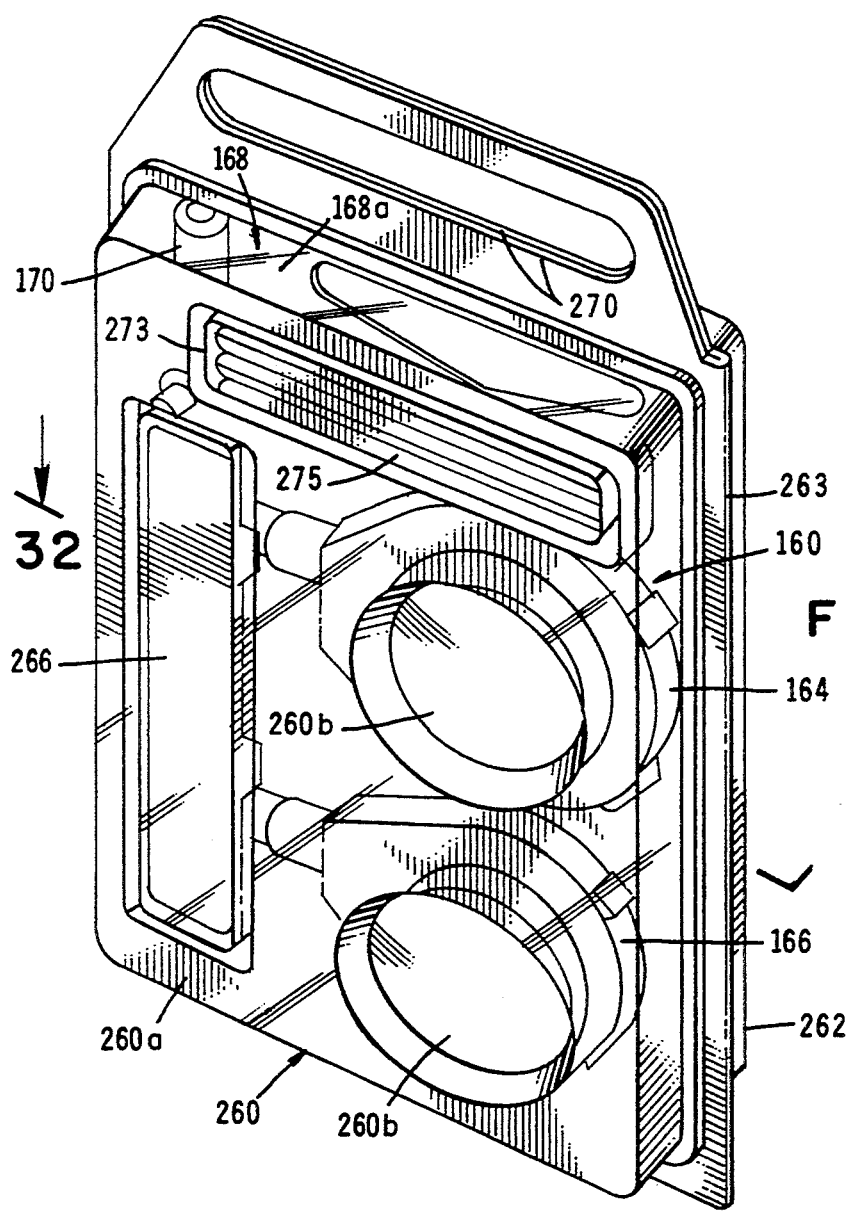
FIG. 31 is a generally perspective view showing the apparatus of FIG. 29 disposed within a sealed transport and storage case.

Referring lastly to FIGS. 31 and 32, a novel transport and storage means is there illustrated. This means, which sealably encapsulates the apparatus of the invention shown in FIG. 25, comprises first and second transparent plastic portions 260 and 262 which are interconnecting by living hinge 263 and which join at their peripheries in the manner best seen in FIG. 32. The opposite side walls 260a and 262a of the casing portions are provided with inwardly extending, curved wall means 260b and 262b for engaging portions 216a of the dispensers so as to hold the delivery apparatus securely in position within the casing for safe transport and storage of the apparatus. Walls 260b and 262b being transparent permit viewing of the position of the distendable membrane to determine whether the reservoirs of the fluid dispensers are full or empty. Pockets 266 are provided in each casing to receive and contain support feet 168c of the platform which feet can be folded into a transport configuration. Similarly, a pocket 273 is provided internally of the casing to receive and contain the fluid administration cannula 275. Additionally, each casing 460 and 262 is provided with finger receiving apertures 270 to permit the assemblage to be easily and safely transported.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery device for delivering fluid at a
    (a) a fluid dispenser including:
        (i) a base having base connector elements provided thereon;
        (ii) stored energy means for forming in conjunction with said base a fluid chamber, said fluid chamber having a fluid inlet and a fluid outlet; and
        (iii) cover means receivable over said base for sealably enclosing said stored energy means; and
    (b) support means for supporting said fluid dispenser including:
        (i) a platform; and
        (ii) mounting means carried by said platform for mounting said fluid dispenser on said support, said mounting means including platform connector elements matable with said base connector elements to interconnect said fluid dispenser with said platform.

2. An apparatus as defined in claim 1 in which said support means further includes a fluid conduit assembly connected to said platform, said fluid conduit assembly having a fluid inlet and a fluid outlet.

3. An apparatus as defined in claim 1 in which said platform connector elements comprise spaced-apart guide rails and in which said base connector elements comprise spaced-apart mounting rails slidably receivable with said guide rails.

4. An apparatus as defined in claim 3 in which said fluid dispenser is connected to said fluid conduit assembly and in which said apparatus further includes locking means for preventing separation of said fluid dispenser from said fluid conduit assembly after said base connector elements have been received within said guide rails.

5. An apparatus as defined in claim 4 in which said locking means comprises a plurality of locking tabs extending from said base of said fluid dispenser and a plurality of locking tabs extending from said platform of said support means.

6. A fluid delivery device for delivering fluids at a controlled rate comprising:
    (a) a fluid dispenser including:
        (i) a base;
        (ii) stored energy means for forming in conjunction with said base a fluid chamber, said fluid chamber having a fluid inlet and a fluid outlet, said stored energy means comprising at least one distensible member, superimposed over said base, said member being distensible as a result of direct pressural contact between said stored energy means and the fluid to be delivered; and
        (iii) cover means receivable over said base for sealably enclosing said stored energy means;
    (b) a platform for supporting said fluid dispenser and mounting means carried on said platform for mounting said fluid dispenser on said platform; and
    (c) filling means for interconnection with said fluid dispenser for filling said fluid chamber of said dispenser with a fluid.

7. A fluid delivery apparatus comprising:
    (a) a fluid dispenser having:
        (i) a base; and
        (ii) stored energy means for forming in conjunction with said base a fluid chamber having an inlet and an outlet, said stored energy means being adapted to controllably expel fluid from said chamber; and
    (b) a support means for supporting said fluid dispenser, said support means comprising:
        (i) a platform;
        (ii) a fluid conduit assembly carried by said platform, said assembly having a fluid inlet and a fluid outlet;
        (iii) mounting means provided on said platform for mounting said fluid dispenser thereon; and
        (iv) connector means for connecting said inlet of said fluid conduit assembly and said outlet of said fluid chamber of said fluid dispenser to permit fluid flow between said fluid dispenser and said fluid conduit assembly.

8. An apparatus as defined in claim 7 in which said fluid conduit assembly includes valve means for controlling the flow of fluid between said fluid chamber of said fluid dispenser and said fluid outlet of said fluid conduit assembly.

9. An apparatus as defined in claim 7 in which said outlet of said chamber of said fluid dispenser includes a pierceable closure membrane and in which said connector means comprises a piercing member for piercing said membrane to provide a fluid passageway between said chamber of said dispenser and said inlet of said fluid conduit assembly.

10. An apparatus as defined in claim 7 in which said outlet of said fluid chamber of said fluid dispenser includes a dispenser valve means for regulating the flow of fluid outwardly of said chamber and in which said connector means comprises valve operating means for operating said dispenser valve means to permit fluid flow between said chamber and said fluid conduit assembly.

11. An apparatus as defined in claim 7 in which said stored energy means comprises a distendable membrane.

12. An apparatus as defined in claim 7 in which said fluid dispenser further includes flow rate control means for controlling the rate of fluid flow from said chamber through said chamber outlet.

13. An apparatus as defined in claim 7 in which said inlet of said chamber of said fluid dispenser includes a septum penetrable by a needle of a syringe.

14. An apparatus as defined in claim 7 in which said base comprises a generally circular dome-shaped member and in which said apparatus further includes cover means, said cover means comprising a generally circular shaped member having a concave central portion.

15. An apparatus as defined in claim 7 further including storage and transport means for sealably enclosing said fluid dispenser and said support means.

16. A fluid delivery apparatus comprising:
 (a) a fluid dispenser having:
  (i) a base;
  (ii) stored energy means for forming in conjunction with said base a fluid chamber having an inlet and an outlet, said stored energy means being adapted to controllably expel fluid from said chamber; and
  (iii) cover means receivable over said base for sealably enclosing said stored energy means; and
 (b) a support means for supporting said fluid dispenser, said support means comprising:
  (i) a platform;
  (ii) a fluid conduit assembly carried by said platform, said assembly having a fluid inlet and a fluid outlet;
  (iii) mounting means provided on said platform for mounting said fluid dispenser thereon; and
  (iv) connector means for connecting said inlet of said fluid conduit assembly and said outlet of said fluid chamber of said fluid dispenser to permit fluid flow between said fluid dispenser and said fluid conduit assembly.

17. An apparatus as defined in claim 16 further including filling means interconnectable with said fluid dispenser for filling said fluid chamber thereof with fluid.

18. An apparatus as defined in claim 17 in which said filling means comprises:
 (a) a container for containing fluid, said container having first and second ends;
 (b) closure means for closing said first end of said container; and
 (c) a plunger telescopically movable within said container from a first position to a second position.

19. An apparatus as defined in claim 18 in which said fluid dispenser includes interconnecting means for interconnecting said filling means with said inlet of said fluid chamber of said fluid dispenser.

20. An apparatus as defined in claim 19 in which said closure means of said filling means comprises a penetrable member and in which said interconnecting means comprises a cannula having a first end adapted to penetrate said penetrable member and a second end in fluid communication with said fluid chamber of said dispenser.

21. An apparatus as defined in claim 20 in which said interconnecting means comprises a plunger engaging means for moving said plunger within said container from said first position to said second position.

22. An apparatus as defined in claim 21 in which said plunger engaging means comprises an elongated stem having a fluid passageway therethrough, said fluid passageway having a first end in communication with said second end of said cannula and a second end in communication with said fluid chamber.

23. An apparatus as defined in claim 21 in which said filling means further includes indicator means for indicating the volume of fluid remaining within said container.

24. A fluid delivery apparatus for controllably delivering fluids to a patient comprising:
 (a) a fluid dispenser having:
  (i) a base;
  (ii) a distendable membrane for forming in conjunction with said base a fluid chamber having an inlet and an outlet, said distendable membrane when distended functions to controllably expel fluid from said chamber; and
  (iii) cover means receivable over said base for sealably enclosing said base and said distendable membrane; and
 (b) support and delivery means for supporting said fluid dispenser and for controllably delivering fluid expelled from said fluid chamber thereof to the patient, said support means comprising:
  (i) a platform;
  (ii) a manifold system carried by said platform, said manifold system having a fluid inlet and a fluid outlet;
  (iii) mounting means provided on said platform for mounting said fluid dispenser thereon; and
  (iv) connector means for connecting said inlet of said manifold system and said outlet of said fluid chamber of said fluid dispenser to permit fluid flow between said fluid dispenser and said manifold system.

25. An apparatus as defined in claim 24 in which said manifold system includes valve means for controlling the flow of fluid between said fluid chamber of said fluid dispenser and said fluid outlet of said manifold system.

26. An apparatus as defined in claim 24 in which said fluid dispenser further includes flow rate control means for controlling the rate of flow of fluids through said outlet of said chamber.

27. An apparatus as defined in claim 24 in which said base includes base connector elements and in which said mounting means of said support and delivery means includes platform connector elements, said platform connected elements being matable with said base connector elements for interconnecting said fluid dispenser with said platform.

28. An apparatus as defined in claim 24 further including filling means for interconnection with said fluid dispenser for filling said fluid chamber of said dispenser with a fluid.

29. An apparatus as defined in claim 28 in which said filling means comprises:
(a) a container for containing fluid, said container having first and second ends;
(b) a closure means for closing said first end of said container; and
(c) a plunger telescopically movable within said container.

30. An apparatus as defined in claim 29 in which said fluid dispenser includes interconnecting means for interconnecting said filling means with said inlet of said fluid chamber of said fluid dispenser.

31. An apparatus as defined in claim 30 in which said closure means of said filling means comprises a penetrable member and in which said interconnecting means comprises a cannula having a first end adapted to penetrate said penetrable member and a second end in fluid communication with said fluid chamber of said dispenser.

32. An apparatus as defined in claim 31 in which said interconnecting means comprises a plunger engaging means for moving said plunger within said container from said first position to said second position.

33. An apparatus as defined in claim 32 in which said plunger engaging means comprises an elongated stem having a fluid passageway therethrough, said fluid passageway having a first end in communication with said second end of said cannula and a second end in communication with said fluid chamber.

34. An apparatus as defined in claim 32 in which said filling means further includes indicator means for indicating the volume of fluid remaining within said container.

* * * * *